(12) United States Patent
Johnson et al.

(10) Patent No.: US 7,815,923 B2
(45) Date of Patent: Oct. 19, 2010

(54) IMPLANTABLE GRAFT MATERIAL

(75) Inventors: Chad E. Johnson, West Lafayette, IN (US); Michael C. Hiles, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 702 days.

(21) Appl. No.: 11/616,159

(22) Filed: Dec. 26, 2006

(65) Prior Publication Data

US 2007/0154515 A1 Jul. 5, 2007

Related U.S. Application Data

(60) Provisional application No. 60/755,279, filed on Dec. 29, 2005.

(51) Int. Cl.
*A61F 2/86* (2006.01)

(52) U.S. Cl. .................. 424/400; 424/422; 435/395

(58) Field of Classification Search .............. 424/400, 424/422
See application file for complete search history.

(56) References Cited

U.S. PATENT DOCUMENTS

| | | | |
|---|---|---|---|
| 3,514,791 A | 6/1970 | Sparks | |
| 4,218,782 A | 8/1980 | Rygg | |
| 4,902,508 A | 2/1990 | Badylak et al. | |
| 4,956,178 A | 9/1990 | Badylak et al. | |
| 5,156,620 A | 10/1992 | Pigott | |
| 5,281,422 A | 1/1994 | Badylak et al. | |
| 5,411,552 A | 5/1995 | Andersen et al. | |
| 5,489,297 A | 2/1996 | Duran | |
| 5,554,389 A | 9/1996 | Badylak et al. | |
| 5,607,465 A | 3/1997 | Camilli | |
| 5,855,601 A | 1/1999 | Bessler et al. | |
| 5,955,110 A | 9/1999 | Patel et al. | |
| 6,096,347 A * | 8/2000 | Geddes et al. | 424/551 |
| 6,099,567 A | 8/2000 | Badylak et al. | |
| 6,110,201 A | 8/2000 | Quijano et al. | |
| 6,126,686 A | 10/2000 | Badylak et al. | |
| 6,168,614 B1 | 1/2001 | Andersen et al. | |
| 6,187,039 B1 | 2/2001 | Hiles et al. | |
| 6,200,336 B1 | 3/2001 | Pavcnik et al. | |
| 6,206,931 B1 | 3/2001 | Cook et al. | |
| 6,287,334 B1 | 9/2001 | Moll et al. | |
| 6,299,637 B1 | 10/2001 | Shaolian et al. | |
| 6,352,555 B1 | 3/2002 | Dzau et al. | |
| 6,358,284 B1 | 3/2002 | Fearnot et al. | |
| 6,454,799 B1 | 9/2002 | Schreck | |
| 6,475,232 B1 | 11/2002 | Babbs et al. | |
| 6,508,833 B2 | 1/2003 | Pavcnik et al. | |
| 6,582,462 B1 | 6/2003 | Andersen et al. | |
| 6,626,823 B1 | 9/2003 | Campbell et al. | |
| 6,716,241 B2 | 4/2004 | Wilder et al. | |
| 6,752,828 B2 | 6/2004 | Thornton | |
| 2001/0011187 A1 | 8/2001 | Pavcnik et al. | |
| 2001/0039450 A1 | 11/2001 | Pavcnik et al. | |
| 2002/0123800 A1 | 9/2002 | Taheri et al. | |
| 2002/0188348 A1 | 12/2002 | DiMatteo et al. | |
| 2003/0036795 A1 | 2/2003 | Andersen et al. | |
| 2003/0130726 A1 | 7/2003 | Thorpe | |
| 2003/0191525 A1 | 10/2003 | Thornton | |
| 2003/0208261 A1 | 11/2003 | Thorpe et al. | |
| 2004/0015230 A1 | 1/2004 | Moll et al. | |
| 2004/0049262 A1 | 3/2004 | Obermiller et al. | |
| 2004/0106991 A1 | 6/2004 | Hopkins et al. | |
| 2004/0193253 A1 | 9/2004 | Thorpe et al. | |
| 2005/0228486 A1 | 10/2005 | Case et al. | |
| 2005/0267560 A1 | 12/2005 | Bates | |

FOREIGN PATENT DOCUMENTS

| | | |
|---|---|---|
| WO | WO 00/23008 | 4/2000 |
| WO | WO 01/10355 | 2/2001 |
| WO | WO 01/19285 | 3/2001 |
| WO | WO 01/37884 | 5/2001 |
| WO | WO 01/78754 | 10/2001 |
| WO | WO 01/85226 | * 11/2001 |
| WO | WO 03/070124 | 8/2003 |
| WO | WO 2004/082528 | 9/2004 |
| WO | WO 2005/011534 | 2/2005 |
| WO | WO 2005/020847 | 3/2005 |
| WO | WO 2005/089673 | 9/2005 |

OTHER PUBLICATIONS

Heeschen, C., et al. "Nicotine Stimulates Angiogenesis and Promotes Tumor Growth and Atherosclerosis". Nature Medicine, vol. 7., No. 7, Jul. 2001. pp. 833-839.

Johnson, C., et al. "Matrix Metalloproteinase-9 is Required for Adequate Angiogenic Revascularization of Ischemic Tissues: Potential Role in Capillary Branching". Circulation Research, vol. 94. (2004) pp. 262-268.

* cited by examiner

*Primary Examiner*—Ruth A Davis
(74) *Attorney, Agent, or Firm*—Woodard, Emhardt, Moriarty, McNett & Henry LLP

(57) ABSTRACT

Described are graft materials suitable for implantation within a patient including isolated tissue material remodeled in a body cavity. Also described are methods of treating a patient that include implanting these materials and prosthetic devices comprising these materials within the patient's body.

53 Claims, 11 Drawing Sheets

IMPLANTABLE GRAFT MATERIAL

REFERENCE TO RELATED APPLICATIONS

The present application claims the benefit of U.S. Provisional Patent Application Ser. No. 60/755,279 filed Dec. 29, 2005 entitled IMPLANTABLE GRAFT MATERIAL.

BACKGROUND

The present invention relates generally to medical devices and methods, and in one aspect relates to a tissue graft material comprising tissue material that has been remodeled in a body cavity and isolated from the body cavity for use. In certain embodiments, the invention provides a prosthetic device, for example, an implantable valve device, comprising such a tissue graft material.

Tissue grafting is one method of medically treating diseased or damaged tissue. One form of tissue grafting is vascular grafting, which can for example be used to repair or replace heart valves or venous valves, or portions thereof, in patients. It is well understood in human pathology that the proper functioning of cardiac and venous valves is of the utmost importance. Numerous studies have shown that diseased cardiac valves cause significant morbidity and mortality and that incompetent or destroyed venous valves often result in adverse medical conditions, especially in the lower extremities.

By preventing retrograde blood flow, the valves found throughout the venous system assist the flow of blood through the veins and returning to the heart. Venous valves are usually of the bicuspid type, with each cusp or leaflet forming a reservoir for blood, which, under pressure, forces the free edges of the cusps together to permit mostly antegrade blood flow to the heart. As a majority of venous blood flow is against gravity while a person is standing, incompetent or destroyed venous valves can cause significant medical problems in the legs, ankles, and feet. There are at least two chronic venous diseases in which venous valve incompetence is thought to be an important factor: chronic venous insufficiency and varicose vein syndrome.

Chronic venous insufficiency involves venous hypertension and chronic venous stasis due to valvular incompetence. It has been estimated that in the United States chronic venous insufficiency associated with skin changes and ulcers affects six to seven million people. Varicose vein syndrome involves vein dilation or enlargement. According to another estimate, varicose veins affect about 4% of the adult western population, and approximately half of this population has significant varicose vein syndrome for which treatment will be sought.

Turning now to the cardiovascular system, incompetent or destroyed heart valves are a common form of heart disease, the leading cause of death in the United States. Although reconstructive surgery has been shown to be superior to valve replacement surgery in some respects, it is difficult to perform and not always possible in every patient. As a result, the vast majority of patients with diseased heart valves undergo valve replacement surgery, which involves removing a native valve and replacing it with a prosthetic one. Prosthetic heart valves come in various shapes and sizes and can be formed with a variety of materials. Often, the design of a prosthetic valve depends on the characteristics of the valve being replaced (e.g., mitral, aortic, tricuspid, or pulmonary) and/or the size of the patient's heart.

A variety of prosthetic valves have been developed in the art to treat conditions of the vascular system. For example, U.S. Pat. No. 6,508,833 discloses a multiple-sided medical device comprising a closed frame of a single piece of wire or other resilient material and having a series of bends and interconnecting sides. The device has both a flat configuration and a second, folded configuration that comprises a self-expanding frame. The device is pushed from a delivery catheter into the lumen of a duct or vessel. A covering of fabric or other flexible material is sutured or attached to the frame to form an artificial valve. The flexible material utilized in the disclosed valves can be comprised of collagenous submucosa obtained from various animals, such as, for example, pigs, cattle, and sheep. The submucosal material can be prepared in large, flat sheets, which are subsequently cut and attached to a framing element, for example a stent, for deployment in a vein.

Apart from vascular applications such as those discussed above, tissue graft materials and techniques have been used to treat a wide variety of diseased or damaged tissues, including for instance musculoskeletal tissues such as bone, ligaments, tendons, and muscles, neural tissues, dermal tissues and many others.

There remain needs for improved and/or alternative graft materials and grafting devices suitable for implantation in the body. The present invention is addressed to those needs.

SUMMARY

The present invention provides, in certain aspects, unique tissue graft material that includes isolated, remodeled tissue material, wherein the tissue remodeling occurred in a location of the recipient's body other than where the graft material is to be implanted, or in a human donor or animal donor other than the recipient. Illustratively, certain embodiments of the present invention relate to graft material comprising isolated, remodeled tissue material, wherein the graft material is configured for implantation within a tubular body passageway, and the tissue remodeling occurred in a body cavity. For example, a prosthetic valve device adapted for implantation within a vascular vessel (e.g., a vein) can comprise isolated tissue material remodeled in a peritoneal cavity. The body cavity can be in the patient being treated, making at least a portion of the isolated tissue material autologous relative to the implant recipient.

In one particular embodiment, the invention provides a tissue graft material suitable for implantation within a patient, the graft material comprising an isolated tissue material remodeled in a body cavity. Any suitable body cavity can be utilized in the invention including but not limited to a peritoneal cavity. Also, the graft material can comprise mesothelial and/or other cells grown in the body cavity. Further, the graft material can have any suitable size, shape, and/or configuration. For example, in certain aspects, the graft material is configured as one or more sheets, tubes or cylinders of material, while in other aspects, the graft material is adapted to provide a particular prosthetic device, such as but not limited to, a valve or a ligament. In a particularly preferred aspect, the graft material is configured as a valve leaflet for implantation within a vascular vessel to treat venous insufficiency. In these and other inventive aspects, the graft material can be grown in substantially its final shape for implant, or can be trimmed or otherwise re-shaped after removal from the body cavity.

In another embodiment, the present invention provides an isolated graft material suitable for implantation, the preparation of which comprises removing from a body cavity of a host a previously inserted amount of remodelable material. The remodelable material is incubated in the body cavity for a period of time sufficient for at least partial remodeling of the remodelable material to occur. In certain aspects, the at least partially remodeled material is removed from the body cavity at least 15 days, but no later than 45 days, after the remodelable material is inserted therein. The amount of remodelable material can be associated with a prosthesis-shaping element (e.g., a form) or other body cavity-insertable element while incubated in the body cavity. Preferably, the amount of remodelable material comprises an extracellular matrix (ECM) material, such as but not limited to, small intestinal submucosa (SIS).

The present invention further provides a prosthetic device suitable for implantation within a patient, the device comprising an isolated tissue material remodeled in a body cavity. The prosthetic device may be adapted to perform any function (or to be implanted anywhere) within the body. For example, in certain aspects, the prosthetic device is configured to provide a prosthetic valve (e.g., a heart valve or a venous valve) for implantation within a body passageway, while in other aspects, the prosthetic device is configured to provide a prosthetic body vessel (e.g., a blood vessel), or a portion thereof, e.g. as in a vascular graft, or to provide an inner lining to a vascular or other body vessel, e.g. a tubular graft used to exclude an aneurism. The prosthetic device may include one or more frame elements, and/or may include one or more adaptations (e.g., barbs or an adhesive) for attaching the device to a site within the patient. Further, any suitable technique and/or instrumentation may be used to implant the prosthetic device within a patient. For example, in certain aspects, the prosthetic valve is deployed within a vein using a percutaneously advancable device such as a catheter.

Another embodiment of the invention provides a medical product that comprises an amount of graft material contained in a sealed package, wherein the graft material comprises isolated tissue material remodeled in a body cavity. The amount of graft material can have any suitable size, shape, and/or configuration. For example, the amount of graft material can comprise one or more pieces or segments of graft material such as that described above, and/or one or more additional elements associated therewith to provide a prosthetic device. In certain aspects, the medical product includes one or more prosthetic valves of the present invention. In other aspects, the product includes one or more tubular grafts of the invention. Also, the product can include suitable instrumentation for implanting the amount of graft material within a patient. Further, the sealed package can be configured to maintain the amount of graft material in a sterile condition when sterilely packaged therein, and can include indicia to communicate information about its contents.

In yet another embodiment, the present invention provides a method of forming an isolated graft material suitable for implantation, which comprises removing from a body cavity a previously inserted amount of remodelable material. In certain aspects, the amount of remodelable material is associated with a body cavity-insertable element (e.g., a form) prior to being inserted into the body cavity, to provide a prosthesis-forming device. After being inserted therein, the prosthesis-forming device is maintained in the body cavity for a period of time sufficient for at least partial remodeling of the remodelable material to occur. Insertion and/or removal of the device can be accomplished in any suitable manner, including but not limited to by open surgery or by potentially less-invasive methods, e.g., laparoscopically. After being removed from the body cavity, the prosthesis-forming device, or any portion thereof, is optionally manipulated to form an implantable prosthetic device. In certain aspects, suitable manipulation includes separating at least a portion of the at least partially remodeled material from the form.

In another embodiment, the invention provides a method of treatment that comprises implanting a prosthetic device in a patient, the device comprising isolated tissue material remodeled in a body cavity. In certain aspects, a percutaneously implantable valve including such a tissue material is deployed within a vascular vessel to treat a condition of the vascular system, e.g., venous insufficiency. In other aspects, a tubular graft is implanted within or as a substitute for all or a portion of a body vessel, e.g. as a vascular graft.

Another embodiment of the invention provides a prosthetic valve suitable for implantation in a patient, the valve comprising isolated tissue material remodeled in a body cavity. Preferably, the body cavity is in the patient being treated, making at least a portion of the isolated tissue material autologous relative to the implant recipient.

Other objects, embodiments, forms, features, advantages, aspects, and benefits of the present invention shall become apparent from the detailed description and drawings included herein.

DETAILED DESCRIPTION

Figure 1:
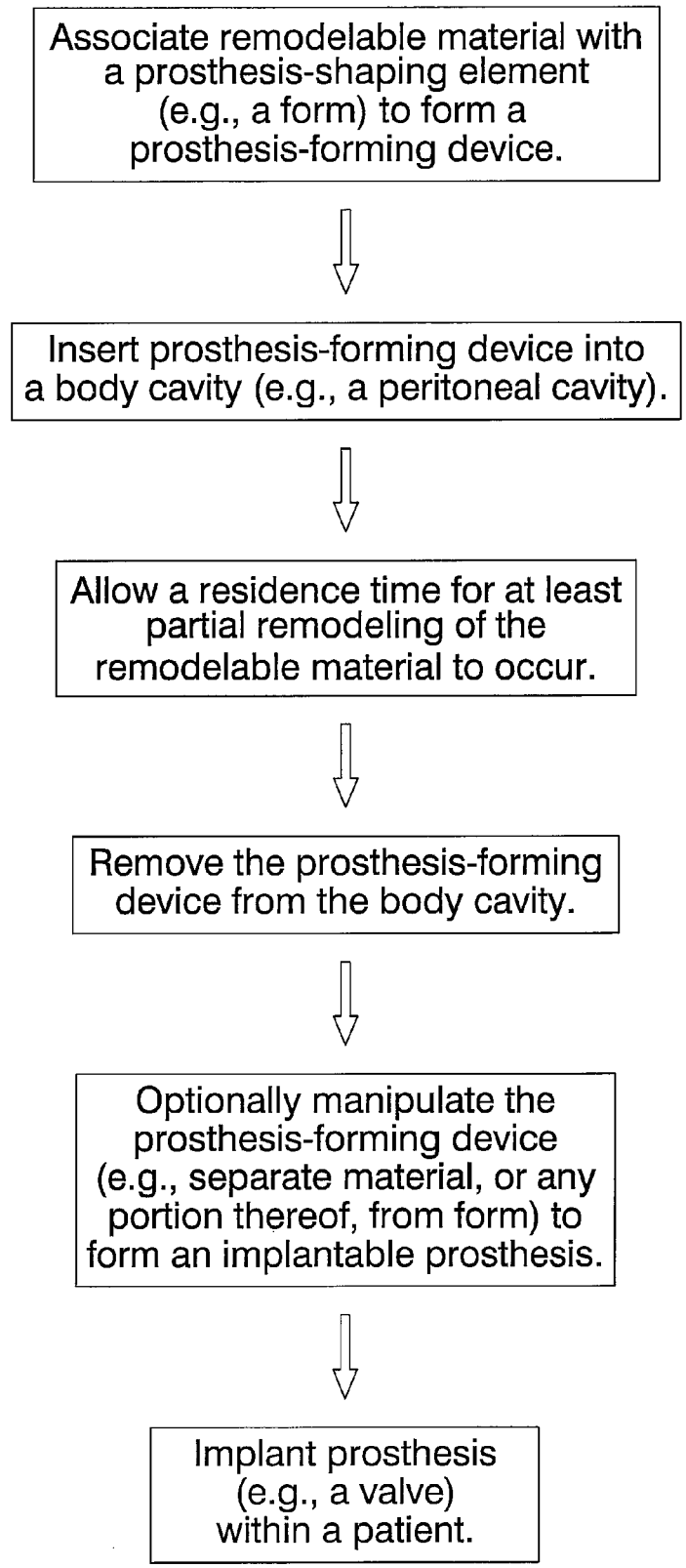
FIG. 1 provides a flow chart depicting one embodiment of the present invention for treating a patient.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, the present invention provides an implantable graft material comprising isolated tissue material remodeled in a body cavity or other body location. In certain embodiments, the invention provides implantable prosthetic devices (e.g., cardiac and venous valves) comprising such a graft material.

With reference now to FIG. 1, shown is a flow chart depicting an embodiment of the present invention for developing a graft material and ultimately treating a patient. As described in greater detail below, this illustrative embodiment includes forming a prosthetic device comprising isolated tissue material remodeled in a body cavity, and thereafter isolating and implanting the device within a patient. In this regard, implanting a prosthetic device in accordance with the present invention avoids having to sacrifice existing, i.e. indigenous, tissue from the implant recipient. In certain aspects, the body cavity is in the patient being treated, making at least a portion of the graft material autologous relative to the implant recipient. In other aspects, the body cavity is in a human or animal donor, making the graft material allogenic or xenogenic, respectively, to the recipient.

In the illustrative embodiment shown in the chart, an amount of remodelable material is associated with a prosthesis-shaping element (e.g., a form) to provide a prosthesis-forming device. However, it should be noted that a prosthesis-forming device of the invention could also be provided by associating an amount of remodelable material with another suitable body cavity-insertable element, such as but not limited to, a frame, a container, or the like. As will be recognized by those skilled in the art, a variety of devices could be associated with an amount of remodelable material for insertion in a body cavity in accordance with the present invention.

When a remodelable material is associated with another inserted object while in the body cavity, the two may or may not remain associated with one another when the remodeled tissue material is later used, for example, when implanting the remodeled tissue material in an implant recipient. Where an object is to remain associated with a remodeled tissue material, this object can have a variety of shapes and sizes, and can be configured to provide a variety of functions at the implantation site. Illustratively, an object of this sort may be one that is adapted for placement at (e.g., inside) a bodily vessel to repair the vessel or otherwise provide benefit to the graft recipient as a result of this placement. Such objects include but are not limited to expandable and non-expandable stents and other similar graft devices known by those skilled in the art. In some forms, a remodelable material is uniquely associated with at least a portion of a stent, for example wherein an outer, remodelable covering material and/or an inner, remodelable covering material contour to and/or embed elements of the stent. These and other suitable implantable objects will be recognized by those skilled in the art, and therefore, are encompassed by the present invention.

Further, an amount of remodelable material can be associated with multiple body cavity-insertable elements, for example, a form and one or more frame elements. In particular, an amount of remodelable material can be attached to or engaged with a form comprising a biodegradable matrix, and a frame comprising a metallic or synthetic polymeric material. In certain embodiments, a first body cavity-insertable element (e.g., a form) is attached to an amount of remodelable material, and the material-form combination is received within a second body cavity-insertable element (e.g., a container). In other embodiments, a remodelable material is associated with a plurality of separate and discrete implantable devices so as to form a unitary device, for example, as described in relation to FIG. 10.

The remodelable material can be associated with the form or other device(s) in any suitable manner, including but not limited to, positioning at least a portion of the material on, around, inside the form, or connecting the material to the form in some manner. For example, in certain embodiments, the amount of remodelable material is held in tension over a mold (or portions thereof). In other embodiments, the amount of remodelable material is sutured to a frame, although it should be noted that various modes of attachment (e.g., staples, adhesives, fasteners, tissue welding or fusion using heat and/or pressure, chemical crosslinking, etc.), alone or in combination, could be used.

Further in this regard, it should be noted that the form and/or the amount of remodelable material can have any suitable size, shape, and/or configuration to provide a graft material or grafting device suitable for implantation within a patient. For example, in certain embodiments, formation of a tubular grafting prosthesis comprises wrapping a sheet of remodelable material concentrically around a tubular or cylindrical mold. In other embodiments, formation of a prosthetic device comprises placing an amount of remodelable material inside a bowl, cylinder, pouch, or pocket-shaped mold, wherein the mold can be configured to shield portions of the material from the body cavity and leave others exposed. In the latter embodiments, at least a portion of the mold may be perforated to allow passage of biological materials such as cells and growth factors therethrough.

The remodelable material of the present invention can be provided by a generally biocompatible and remodelable extracellular matrix (ECM) material. Suitable ECM material of the present invention can be derived from a variety of natural sources, including pericardial tissues (e.g., pericardial sacs), amniotic membrane, connective tissues, blood vessels, cartilage, dura mater, skin (e.g., dermal collagen), fascia, umbilical tissues, renal capsule membrane, serosa, peritoneum, basement membrane materials (e.g., liver basement membrane), submucosa and the like. Suitable remodelable materials can be derived from a variety of animal species, typically mammalian, such as human, bovine, equine, ovine, or porcine. The submucosal tissue of cattle, sheep, and other warm-blooded vertebrates, especially pigs, provides a particularly preferred material for use in the present invention. These materials may include a portion of an organ or structural tissue components of an organ. Suitable remodelable tissue is typically soft tissue. In some instances, bioremodelable materials are provided by collagenous ECM materials possessing biotropic properties, including in certain forms angiogenic collagenous extracellular matrix materials such as submucosa. Suitable submucosa materials for these purposes include, for instance, intestinal submucosa, including small intestinal submucosa, stomach submucosa, urinary bladder submucosa, and uterine submucosa.

While submucosa or other ECM materials of the present invention can be derived from any suitable organ or other tissue source, they are usually derived from sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers.

When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Submucosal or other graft ECM tissue may, for example, be prepared as described in U.S. Pat. Nos. 4,902,508; 5,554,389; and 6,206,931. Again, it should be understood that when used, ECM material can be derived from any suitable organ or other biological structure, including for example, from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. Thereafter, the submucosa or other ECM material can be assembled into tissue segments (e.g., sheets, strands, and other shapes) or stored for later processing.

Tissue ingrowth-receptive material that can be used in certain aspects of the invention may also be derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

The remodelable ECM or other tissue-ingrowth receptive material may be manipulated before or after it is assembled into a component of the present invention. For example, the material may be cut, trimmed, sterilized, and/or treated with one or more property modifiers. In certain embodiments, an ECM material is crosslinked before or after any preliminary processing and/or storage. Crosslinking tends to fix ECM material in the shape imposed during the crosslinking process. However, because certain crosslinking agents and/or certain degrees of crosslinking can impair or destroy the remodelable properties of a remodelable material, where preservation of remodelable properties is desired, any crosslinking of the remodelable ECM material can be performed to an extent or in a fashion that allows the material to retain at least a portion of its remodelable properties. Following any crosslinking, the material can be further processed, which can involve additional chemical and/or mechanical manipulation of the material, as well as processing the material into the desired invention component.

Crosslinking, can be introduced by any of a variety of agents known therefor. Glutaraldehyde, formaldehyde, epoxides, epoxyamines, diimides and other difunctional/polyfunctional aldehydes can be used, as examples. In particular, aldehyde functional groups are highly reactive with amine groups in proteins, such as collagen. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound.

In addition to being crosslinked, the ECM material can be treated (e.g., brought into contact, impregnated, coated, etc.) with one or more desirable compositions, such as anticoagulants (e.g., heparin), growth factors, other desirable property modifiers, and the like to modify the tissue properties. The ECM material can be treated with an anticalcification agent to reduce calcification of the tissue following implantation. Generally, any calcification reducing agents would be contacted with the ECM material following crosslinking, although some calcification reducing agents can be contacted with the tissue prior to crosslinking. Suitable calcification reducing agents include, for example, alcohols, such as ethanol and propylene glycol, detergents (e.g., sodium dodecyl sulfate), toluidine blue, diphosphonates, and multivalent cations, especially $Al^{+3}$, $Mg^{+2}$ or $Fe^{+3}$, or corresponding metals that can oxidize to form the multivalent metal cations.

Additionally, to encourage ingrowth of viable cells, the ECM material can be treated to reduce or eliminate toxicity associated with aldehyde crosslinking and/or associated with compounds that stimulate the infiltration of the tissue by desirable cells. Suitable compounds for reduction of aldehyde cytotoxicity include, for example, amines, such as amino acids, ammonia/ammonium, sulfates, such as thiosulfates and bisulfates, surfactants and combinations thereof.

As prepared, the ECM material may optionally retain various bioactive components native to the source tissue. For example, the ECM material may include one or more growth factors, such as basic fibroblast growth factor (FGF-2), transforming growth factor beta (TGF-beta), epidermal growth factor (EGF), cartilage derived growth factor (CDGF) and/or platelet derived growth factor (PDGF). Further, the submucosa or other ECM material of the present invention may include other native biological materials, such as heparin, heparin sulfate, hyaluronic acid, fibronectin and the like. Thus, generally speaking, the ECM material may include a native or endogenous bioactive component that induces, directly or indirectly, a cellular response, such as a change in cell morphology, proliferation, growth, protein or gene expression.

In addition to, or as an alternative to, the inclusion of such native bioactive components, non-native bioactive components, such as those synthetically produced by recombinant technology or other methods, may be incorporated into the ECM material, or into another tissue ingrowth-receptive material. The incorporation of a non-native component, e.g., a growth factor, with a the ECM or other tissue receptive material may involve direct attachment, application of a coating, including an adhesive or binder, or chemical bonding such as covalent bonding methods.

The present invention also provides, in certain aspects, materials having one or more cell populations added thereto. In some embodiments, one or more exogenous cell populations are added to a remodelable material before it is inserted into a body cavity for remodeling. Additionally or alternatively, exogenous cells can be incorporated into a remodeled tissue material after it is removed from the body cavity but before it is implanted within an implant recipient.

Additional cells utilized in the invention include human and non-human animal cells. When cells are added to a remodeled material after it is removed from the body cavity but before it is implanted in a human implant recipient, these added cells are preferably human cells. Nonetheless, any additional cells, regardless of when they are added to a material, may be autologous to the eventual implant recipient, allogenic to the implant recipient, or xenogenic to the implant recipient. The cells may be derived and potentially expanded from biopsy tissue, or may be derived from stable cell lines, including human cell lines.

Cells may be seeded onto a material using any suitable methods. In this regard, when more than one cell type is to be seeded, the various cell types can be seeded onto the material together, or separately. This seeding process may occur at any time, for example, any time up to the insertion of the remodelable material in the body cavity and/or any time up to the implantation of the remodeled tissue material in the implant recipient. The seeding process may involve the expansion of the cells prior to insertion and/or implantation, or may lack any such expansion. Moreover, one cell type may be expanded, whereas another may not. When expanding or otherwise culturing cells, suitable culture conditions may be used as known in the art.

An additional exogenous cell population may be any cell population adding to the functional characteristics or durability of a material. Illustratively, a given cell type added to a remodelable material may be selected to influence the types of cells that will be present in the material upon remodeling of the material. In one embodiment of the present invention, an additional exogenous cell population includes endothelial cells, or precursors thereto, which can be derived from any suitable source of endothelial cells including vascular endothelial cells from arterial or venous tissues. Other suitable cell types include muscle cells or precursors to muscle cells. Smooth muscle cells or their precursors are preferred. Suitable muscle cells and precursor cells for use in the invention are disclosed, for example, in WO 178754, published Oct. 25, 2001.

In certain embodiments, additional cells include fibroblasts, or precursors thereto. In still a further preferred embodiment, endothelial cells, preferably vascular endothelial cells, fibroblasts, and smooth muscle cells (or precursors to any of these cells) are all seeded onto a graft material. In some forms, tissue graft constructs of the invention take the form of a tubular construct, wherein cells may be seeded onto the interior (lumenal) surface, the exterior surface, or both. Illustratively, in accordance with one preferred embodiment of the invention, the lumenal surface of a tubular construct can be populated with endothelial cells, preferably vascular endothelial cells. At least one additional exogenous cell population, preferably muscle cells such as smooth muscle cells, and/or fibroblasts, can also be included on the construct. Such tissue grafts provide advanced functionality and durability beneficial to replacement vessels for use in patients, including human patients.

ECM material used in the invention is preferably highly purified, for example as described in U.S. Pat. No. 6,206,931. Thus, the preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, and more preferably less than about 0.5 CFU per gram. Fungus levels are desirably low as well, for example less than about 1 CFU per gram, and more preferably less than about 0.5 CFU per gram. Nucleic acid levels are preferably less than about 5 $\mu$g/mg, and more preferably less than about 2 $\mu$g/mg, while virus levels are preferably less than about 50 plate forming units (PFU) per gram, and more preferably less than about 5 PFU per gram. These and additional properties of ECM material taught in U.S. Pat. No. 6,206,931 may be characteristic of the ECM material used in the present invention.

Accordingly, in some aspects of the invention, a remodelable material is sterilized or otherwise purified before it is inserted into a body cavity for remodeling. Additionally or alternatively, the resulting remodeled tissue material may be similarly treated after it is removed from the body cavity but before it is implanted within the implant recipient. In some forms of the invention, preparation of a graft material involves retrieving a remodeled tissue material from a body cavity in which it was inserted for remodeling, and thereafter treating this material so as to substantially remove or at least kill the cells associated therewith. Thereafter, one or more cell populations can be added to this material as described above.

Continuing with FIG. 1, after the prosthesis-forming device is assembled, the device is inserted into a body cavity. Insertion of the prosthesis-forming device can be accomplished in any suitable manner. In this regard, any suitable invasive, non-invasive, or minimally invasive technique and/or instrumentation can be employed. For example, in certain embodiments, a prosthesis-forming device is inserted into a body cavity laparoscopically, while in other embodiments, the same is accomplished via open surgery. The prosthesis-forming device may be inserted into the body cavity so that it is effectively placed without restraint in the cavity, i.e., it is "free floating." Alternatively, the device is fixed to a region within the body cavity, which may make insertion and/or removal of the device easier.

Any suitable body cavity may be used including but not limited to the peritoneum, thoracic cavity, scrotum, brain, joint or pericardial cavity. A suitable body cavity or other site will generally be one in which the remodelable material can at least partially remodel. In some cases, a particular site is selected to take advantage of one or more conditions occurring at the site which will affect the manner in which the material remodels (e.g., conditions affecting the rate at which a material remodels, the type and/or quality of remodeling that occurs, etc.). Preferably, the body cavity is lined with mesothelial cells. In a preferred aspect, a prosthesis-forming device is inserted into a peritoneal cavity with a laparoscope. The peritoneal cavity is preferred in accordance with the present invention, because it is relatively easy to access and generally less-disruptive to the host.

The amount of remodelable material can be associated with the form or other body cavity-insertable element before or after being inserted into the body cavity. For example, in certain embodiments, an amount of remodelable material is placed inside a perforated container that was previously inserted into a body cavity. Nonetheless, it should be understood that an amount of remodelable material of the present invention need not be associated with a body cavity-insertable element at all while inside the body cavity.

After being inserted therein, the prosthesis-forming device is maintained in the body cavity for a period of time sufficient for at least partial remodeling of the remodelable material to occur. (Hereinafter, this period of time will be referred to as a "residence time.") A favorable characteristic of remodelable material and in particular remodelable submucosal tissue (e.g., small intestinal submucosa, stomach submucosa, urinary bladder submucosa, or uterine submucosa) is that it has the capacity to induce host tissue proliferation and lead to the remodeling and regeneration of tissue structures upon in vivo insertion and/or implantation. In this respect, remodeling of the amount of remodelable material can include infiltration of the material by cells (e.g., mesothelial cells) within the body cavity.

In certain embodiments, remodeled material of the invention includes granulation tissue formed on the remodelable material, wherein the shape and/or configuration of the remodelable material influences the shape and/or configuration of the granulation tissue formed. In this regard, granulation can form on, around, or within the remodelable material, or any portion thereof, or can otherwise be incorporated into or engaged with the remodelable material in some manner, and thereby take the form of the shape of the amount of remodelable material, or portions thereof. This granulation tissue can include cells involved in an inflammatory response. For example, the granulation tissue can include granulocytes, macrophages, and/or stromal cells. Such tissue can also include myofibroblasts and/or mesothelial cells.

The residence times of the present invention can be varied depending on any number of factors, including but not limited to, the degree of remodeling that will occur under the circumstances of the insertion and incubation of the remodelable material. It should be noted that various residence time schedules can be designed through routine experimentation so as to allow a desired degree of tissue remodeling. In preferred aspects, the material on which the new tissue is to be formed is maintained inside the body cavity for at least 1 week, for example up to about 12 weeks, and in certain aspects for at least 2 weeks but no longer than 6 weeks. After a desired residence time, the prosthesis-forming device is removed from the body cavity. Any suitable instrumentation and/or technique may be used to remove the device, including but not limited to those herein disclosed for inserting the device.

After being removed from the body cavity, the prosthesis-forming device is optionally manipulated to form a prosthetic device suitable for implantation within a patient. The prosthesis-forming device can be manipulated in any suitable manner, including but not limited to, cleaning, sterilizing, and/or performing any manner of chemical, biological, and/or physical alteration of, the device, or any portion thereof. For example, in preferred embodiments, manipulation includes separating the at least partially remodeled material, or portions thereof, from the form. In these embodiments, the separated material, or portions thereof, can then be adapted for implantation as one or more prosthetic devices, e.g. a valve leaflet. Any suitable technique and/or instrumentation can be used to separate the material from the form, such as but not limited to cutting with a scalpel or other sharp instrument, manual separation, and the like.

Further in this regard and whether or not still attached to the form, the at least partially remodeled material, or portions thereof, can be associated with one or more additional structures, such as frame elements, before of after being implanted within a patient. For example, the material can be associated with one or more removable frame elements as described in International Patent Application Serial No. PCT/US2004/008176 filed Mar. 17, 2004, published Sep. 30, 2004, as W02004/082528, which is hereby incorporated by reference. For example, a prosthetic valve device including one or more removable frame elements and an amount of at least partially remodeled material of the invention can be implanted (e.g. percutaneously) in a bodily passageway of a patient, such as a vein or artery, allowed to indwell for a sufficient period of time to achieve local tissue ingrowth or integration into the valve (e.g., for site fixation and/or sealing), and the removable frame element(s) thereafter retrieved (e.g. percutaneously). The resulting long-term valve in the patient can thereby include fewer or no associated frame elements.

Additionally, an implantable graft material or grafting device of the present invention may include one or more adaptations to suitably anchor the same within a patient. For example, in certain embodiments where a prosthetic valve is formed, one or more vessel-attaching elements (e.g., barbs) are attached to or incorporated into the valve to attach the same to a vessel wall. In addition to barbs, suitable adaptations can include any device or material that facilitates attachment to a vessel wall, such as but not limited to adhesives, hooks, and the like. Also, these adaptations can be associated with the graft material or grafting device before or after the same is implanted within a patient.

Continuing with FIG. 1, the illustrative embodiment further includes implanting the prosthesis within a patient as a method of treatment. Implantation can be accomplished in any suitable manner including percutaneously laproscopically or via open surgery. In preferred embodiments, a prosthetic valve comprising graft material of the invention is implanted within a vascular vessel to treat venous reflux. In other preferred embodiments, a tubular graft comprising graft material of the invention is configured for implantation within a patient as a vascular graft.

While the graft material of the present invention suitable for grafting within the vasculature, the present invention extends to the use of the graft material elsewhere in the body. For example, in certain embodiments, graft material of the invention is adapted for implantation within a patient to augment, support or restore soft tissue, and in other embodiments, to provide a prosthetic ligament or tendon device.

Suitable remodelable material to be inserted can include xenografts (i.e., cross species, such as a non-human donor for a human recipient), allografts (i.e., interspecies with a donor of the same species as the recipient) and/or autografts (i.e., the donor and the recipient being the same individual) relative to the human or other animal in which the remodeled tissue material will be grown for isolation. As well, isolated graft material in accordance with the present invention (i.e. graft material comprising isolated tissue material remodeled in a body cavity) can include xenografts, allografts, and/or autografts relative to the implant recipient. For example, in one embodiment, an amount of remodelable material extracted from a porcine animal is inserted into a body cavity of a human host, making the inserted remodelable material a xenograft. After at least a portion of the remodelable material has been remodeled (e.g., infiltrated and replaced by cells of the host), the material is removed from the body cavity. Thereafter, the graft material is implanted in the same human. In another embodiment, a remodelable material is inserted into a non-human animal, such as a porcine animal, as an autograft, allograft, or xenograft. After a residence time in such animal, a remodeled tissue material is recovered, decellularized, sterilized and implanted in a human as a xenograft. In some instances, such a remodeled tissue material is further populated with one or more autologous cell populations prior to being implanted in the patient.

It should be noted that the terms "insert", "inserting", and "inserted" are used herein to refer to portions of the application generally involving the placement of an object (e.g., a segment of remodelable material) in a body cavity to facilitate the formation of a graft material or grafting device of the present invention. On the other hand, the terms "implant", "implanting", "implanted", "implantation", and "implantable" are used herein to refer to portions of the application generally involving the later placement of a graft material or grafting device of the present invention somewhere in the body (e.g., within a vein). Therefore, while the terms could be used to describe either scenario, they are segregated in the present application solely for the sake of clarity.

Figure 2A:
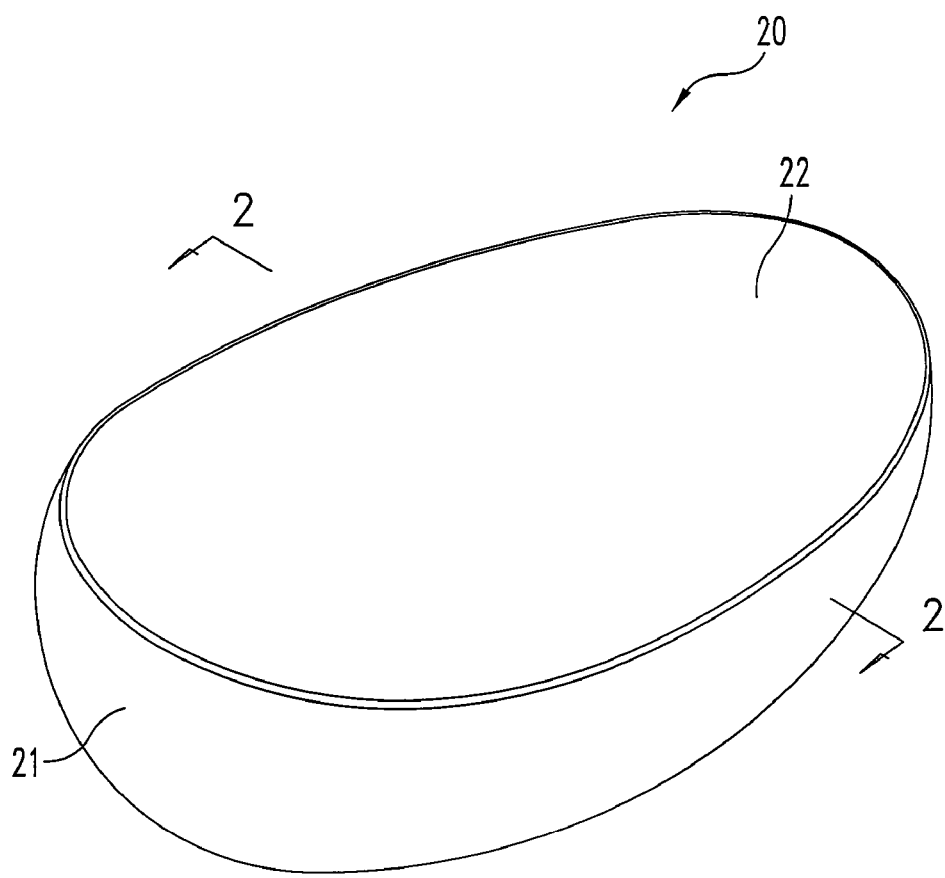
FIG. 2A provides a perspective view of one prosthesis-forming device of the present invention.

The graft material of the present invention can be adapted to provide any grafting device suitable for implantation within a patient including but not limited to a shaped valve cusp. With reference now to FIG. 2A, shown is a perspective view of an illustrative prosthesis-forming device 20 of the invention, which includes a relatively thin sheet of remodelable material 21 attached to a cusp-shaped mold 22. The size, shape, and/or configuration of the cusp-shaped mold 22, as well as the sheet of remodelable material 21, can be varied to provide a prosthetic cusp having any suitable dimensions.

Figure 2B:
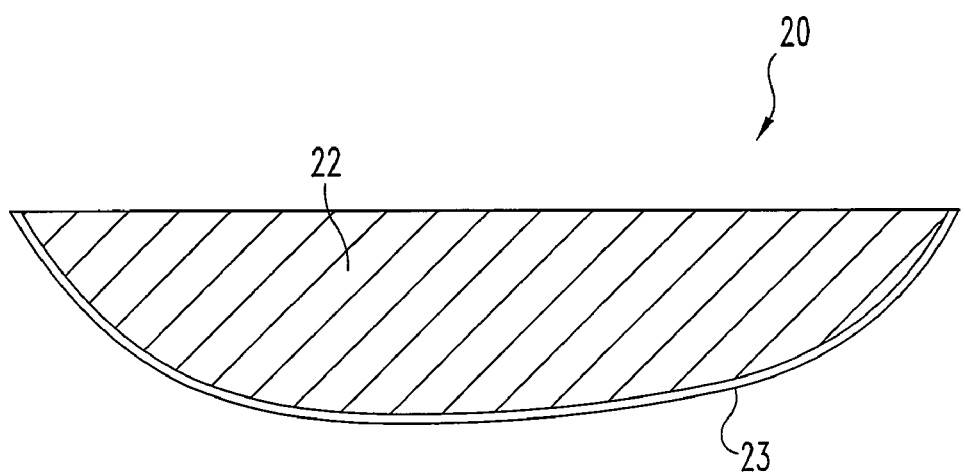
FIG. 2B provides a front view of the device of FIG. 2A along the view line 2-2 shown in FIG. 2A.

As before, the prosthesis-forming device 20 is inserted into a body cavity for a period of time sufficient for at least partial remodeling of the remodelable material 21 to occur. As the material remodels, portions of the sheet of material in contact with the mold 22 become remodeled in the shape of the cusp-shaped mold 22. In preferred embodiments, the at least partially remodeled material retains the general shape of the mold 22, yet remains flexible, when separated therefrom. After a suitable residence time, the prosthesis-forming device 20 is removed from the body cavity, and optionally manipulated to form an implantable prosthetic cusp. FIG. 2B shows a cross-sectional view of the prosthesis-forming device 20 including at least partially remodeled material 23.

Graft material of the present invention can be adapted to provide any valve suitable for implantation within a body passageway of a patient. For example, graft material of the invention can be adapted to provide a monocusp valve in a vascular vessel, or, alternatively, it can be adapted to provide for a multicuspid valve in a vascular vessel, wherein the multicuspid valve comprises a plurality of cusps. In this respect, the graft material can be adapted to provide a bicuspid valve, a tricuspid valve, or a quadracuspid valve in a vascular vessel, wherein any of these valves may or may not include one or more frame elements.

When a monocusp valve configuration is utilized in the invention, the graft material having such a configuration can be dimensioned and attached to the vessel in such a manner so as to allow the cusp to extend across the entire lumen of a vessel and co-apt with the opposite wall of the vessel. Alternatively, two or more prosthetic cusps can be provided and dimensioned for separate attachment to the wall of the vessel so as to co-apt with each other within the vessel lumen, e.g. near the middle of the lumen. When a multicusp valve configuration is utilized, the valve will comprise at least two cusps, wherein the at least two cusps are attached to the vessel wall in such a manner so as to allow the cusps to move inwardly and outwardly within the lumen of the vessel so as to result in a valving action.

A prosthetic cusp of the invention can be deployed within a vessel in any suitable manner. For example, in certain embodiments, the cusp is attached to walls of the vessel in an open surgery procedure. Such a procedure may comprise suturing or otherwise physically connecting portions of the cusp to the luminal surface of the vessel. Other potential attachment procedures include, for example, stapling, bonding or otherwise adhering portions of the cusp to the luminal surface of the vessel. In other embodiments, a prosthetic cusp of the invention is deployed within a vessel percutaneously, e.g., using a suitable delivery device such as a catheter. A catheter can be delivered to the treatment site using any suitable delivery technique, such as but not limited to tracking an emplaced guidewire.

Further in this regard, a number of potential attachment paths are contemplated as within the scope of the present invention. For example, when a bicuspid configuration is utilized, the edges of the cusps can extend in a direction generally both longitudinally and circumferencially around the vessel wall. Also, the cusps can be attached to the vessel wall in any suitable manner including but not limited to utilizing mechanical elements, sutures, bonding, welding, or the like.

A prosthetic cusp of the invention can be constructed so as to have predetermined dimensions. For example, a cusp can be adapted to provide a valve function in a vein or other vessel of a specific diameter. In certain embodiments, the dimensions of the cusp can be selected so as to render the cusp suitable for providing a valve function in a vein or other vessel having an inner diameter of about 5 mm to about 25 mm, more typically in the range of about 8 mm to about 20 mm.

The invention also provides a prosthetic cusp product line. In certain embodiments, a prosthetic cusp product line comprises a plurality of packaged, sterile cusps such as those described herein, wherein the plurality of cusps includes packaged cusps of varying dimensions to suit varying patients or applications. For example, a product line including at least 3 differently dimensioned products, more typically about 3 to about 20 differently dimensioned products, is contemplated as within the scope of the present invention.

Where the prosthetic cusp is to be used to provide a venous valve, the valve can be implanted above, below, or at the location of a native venous valve in the patient. Moreover, a plurality of the valves can be implanted in a given vein, to treat venous insufficiency or other similar disorders.

Figure 3A:
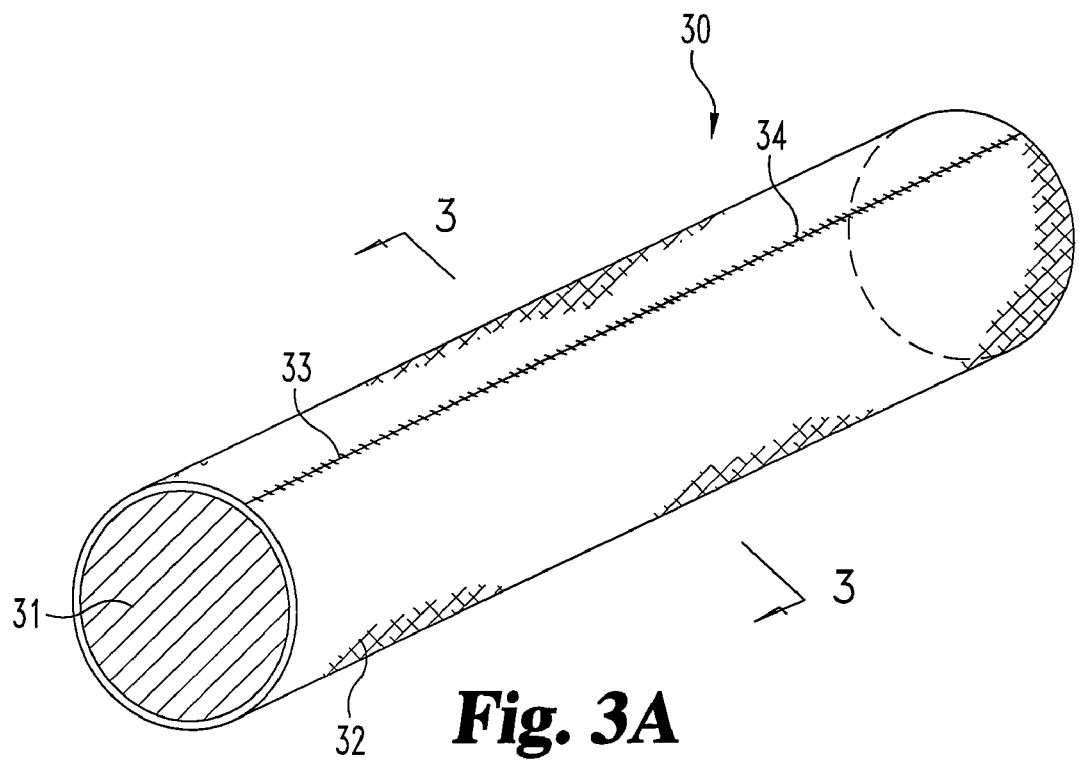
FIG. 3A provides a perspective view of another prosthesis-forming device of the present invention.
Figure 3B:
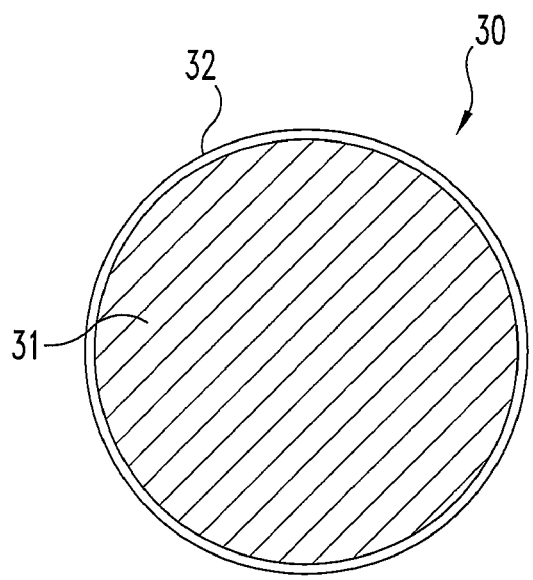
FIG. 3B provides a front view of the device of FIG. 3A along the view line 3-3 shown in FIG. 3A.

Again, the graft material of the present invention can be adapted to provide any grafting device suitable for implantation within a patient, including but not limited to a tubular grafting device. A tubular grafting device of the invention can be adapted to replace a circulation vessel, or a portion thereof, or to bypass a blocked vessel, or to line a vascular or other vessel, for example, a vein or an artery. With reference now to FIGS. 3A and 3B together, shown are a perspective view and a cross-sectional view, respectively, of an illustrative prosthesis-forming device 30 of the present invention, which includes a generally cylindrical form 31 received concentrically within a tube of remodelable material 32. As described below, this device can be inserted into a body cavity as a step in providing a tubular graft comprising remodeled material. (Here, the phrase "generally cylindrical" is meant to include objects that have approximately the same cross-sectional area throughout their length and/or width.) The present invention also provides tubular grafting devices which are not generally cylindrical, but are otherwise desirably shaped, e.g., having a conical portion.

As before, the prosthesis-forming device 30 can be inserted into a body cavity for a period of time sufficient for at least partial remodeling of the remodelable material 32 to occur. The tube of remodelable material 32 depicted in FIGS. 3A and 3B can be formed by connecting opposing sides of a generally rectangular sheet of remodelable material, and therefore, has a seam 33. Nonetheless, it should be noted that a seamless tube of remodelable material could be used as well. Also, while the tube 32 is held together with sutures 34, other modes of attachment (e.g., adhesives, fasteners, laser or other tissue welding or fusion using heat and/or pressure, chemical crosslinking, dehydrothermal bonding etc.), alone or in combination, are contemplated as within the scope of the present invention.

Continuing with FIGS. 3A and 3B, as the material remodels, it does so in the shape of the form 31, such that the material retains a tubular shape after being separated from the form. Also, the remodeling of the material promotes tissue ingrowth into the seam 33 to provide a tissue bond between opposing sides of the sheet. In preferred embodiments, the extent of remodeling is such that the resulting tubular tissue is effectively seamless and thus the sutures can be removed, dissolved, etc.

After a suitable residence time, the prosthesis-forming device 30 is removed from the body cavity (and optionally manipulated) to form a grafting device suitable for implantation within a patient. In preferred embodiments, manipulation includes separating at least a portion of the at least partially remodeled material from the form 31 to provide a tube of graft material. In these embodiments, the tube can be further manipulated, for example, by everting the tube, trimming portions of the tube, decellularizing, sterilizing, packaging and/or associating other structures with the tube, such as but not limited to one or more frame elements and/or one or more anchoring elements. Illustratively, an isolated tube of remodeled tissue material can be attached to or otherwise associated with a stent, valve, plug or other implantable device known to those skilled in the art for placement within a bodily vessel or other similar bodily opening to provide treatment to a patient. In addition, the tube of graft material can be formed having additional internal or external features, by including adaptations on the implanted form to develop such features. Illustratively, a remodeled tubular graft having one or more integrally-formed internal valves can be formed, e.g. monocuspid, bicuspid, tricuspid or other multicuspid valve(s), by providing such features on the form device that is implanted in the bodily cavity. In certain embodiments, features that are desired to occur internally within the remodeled tubular graft, e.g. valve(s) features, can be formed externally on a form, and the resulting remodeled graft can be separated from the form and everted to provide the desired internal features. In a similar fashion, features desired upon an external surface of a tubular graft can be formed internally on the implanted form, and the remodeled graft harvested and everted to provide the features externally.

In certain embodiments, a mold (e.g., a tubular mold) remains part of a prosthetic device (e.g., a prosthetic vessel) provided for implantation. In these embodiments, the mold may be a biodegradable matrix. In other embodiments, a prosthesis-forming device comprises an amount of remodelable material associated with a biodegradable matrix element and a mold. In these embodiments, after the prosthesis-forming device is removed from the body cavity, the biodegradable matrix element and the at least partially remodeled material, or portions thereof, can be separated from the mold, wherein the biodegradable matrix generally remains associated with the later implanted device until it dissolves or breaks down. In this regard, it will be understood that when used in this fashion, the biodegradable, matrix will be formulated to essentially completely or at least partially survive the residence period intact, but degrade over time when ultimately implanted in the recipient.

Additionally, it will be understood that the graft devices described herein can include remodeled tissue material in single- and multilayered form. In some instances, individual layers of remodelable material are remodeled in a body cavity and then combined with one another to form a multilayered remodeled material construct. In other instances, two or more layers of remodelable material are associated with one another before being inserted into a body cavity for remodeling. In these various devices, a layer of remodeled material can exhibit any suitable size and shape. When a device includes more than one layer of remodeled material, these various layers can be arranged in any suitable manner relative to one another.

In some instances, an amount of remodelable material insertable into a body cavity for remodeling includes a plurality of ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. Any two layers can partially or fully overlap one another. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously pressing the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In certain embodiments, a tube of material useful in the invention has walls formed with one or more layers of remodelable extracellular matrix material, for example including one to about four or more layers of remodelable extracellular matrix material. When a wall includes multiple material layers, these layers may be bonded to one another by any suitable method including but not limited to the use of biocompatible adhesives such as collagen pastes, fibrin glue, and the like. Layers may also be debydrothermally bonded to one another, for example by compressing overlapped regions under dehydrating conditions. To prepare tubular graft constructs of the invention, flat sheet extracellular matrix materials can be configured to a tubular form in any suitable manner. These include, for example, techniques in which a flat sheet of extracellular matrix material is configured into a tube shape, and sutured or otherwise bonded to retain the tube shape. Suitable methods for forming tubes of collagen tissues are disclosed in U.S. Pat. Nos. 6,187,039, 6,206,931; and 6,358,284, and in WO 0110355 published Feb. 15, 2001. Such tubes can be inserted into a body cavity to be remodeled essentially by themselves, or alternatively, in combination with one or more other insertable objects.

Figure 4A:
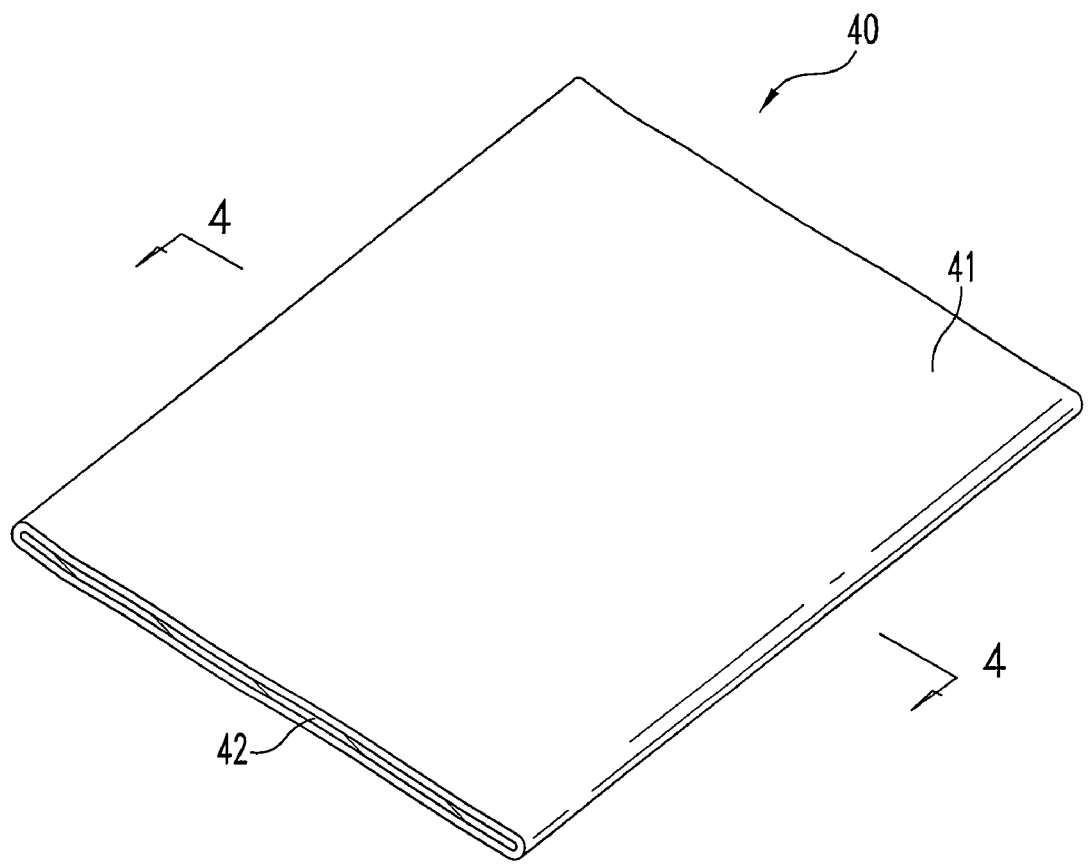
FIG. 4A provides a perspective view of a graft-forming device of the present invention.
Figure 4B:
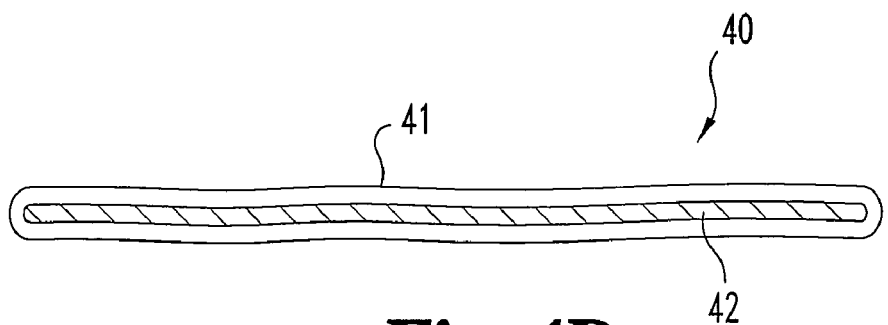
FIG. 4B provides a front view of the device of FIG. 4A along the view line 4-4 shown in FIG. 4A.

FIGS. 4A and 4B provide a graft-forming device 40 of the present invention, wherein a seamless band of remodelable material 41 is stretched taut around a generally planar form 42. It should be noted that the degree of tautness can affect the degree and/or the type of remodeling that occurs. Accordingly, different degrees of tautness can be designed through routine experimentation so as to allow for advantageous material remodeling. Like before, the graft-forming device 40 can be inserted into a body cavity, and thereafter removed and optionally manipulated to provide a graft material in accordance with the present invention.

The current embodiment is particularly useful for forming sheets of graft material that can later be adapted to provide any grafting device suitable for implantation within a patient. In some instances, these and other sheet-form materials of the invention are used as sheet-form products for grafting purposes, for example, as hernia patches, wound care patches or other tissue support and/or repair devices. In other instances, such materials are manipulated to form non-sheet-form devices such as but not limited to tubes, plugs, etc. Additionally or alternatively, a sheet-form construct can be combined with one or more other implantable devices and/or materials including any of those described herein. In this regard, the size, shape, and/or configuration of the graft-forming device 40 may or may not be selected with a particular grafting device in mind. Accordingly, the dimensions of the mold 42 and/or the band 41 can be varied to provide sheets of any desired size, shape, and/or configuration. In certain embodiments, one or more sheets of graft material of the invention are adapted for implantation in a procedure occurring shortly after (e.g., within 24 hours) the sheets are provided, while in other embodiments, one or more sheets are processed and sterilely packaged for later use. In general, an isolated sheet-form material according to the invention can be treated or otherwise suitably processed or handled in any suitable manner prior to being implanted within a patient. These can include a variety of physical, chemical, biological and/or other treatments including any of those described herein (e.g., sterilization, addition of a bioactive agent, etc.)

Figure 5A:
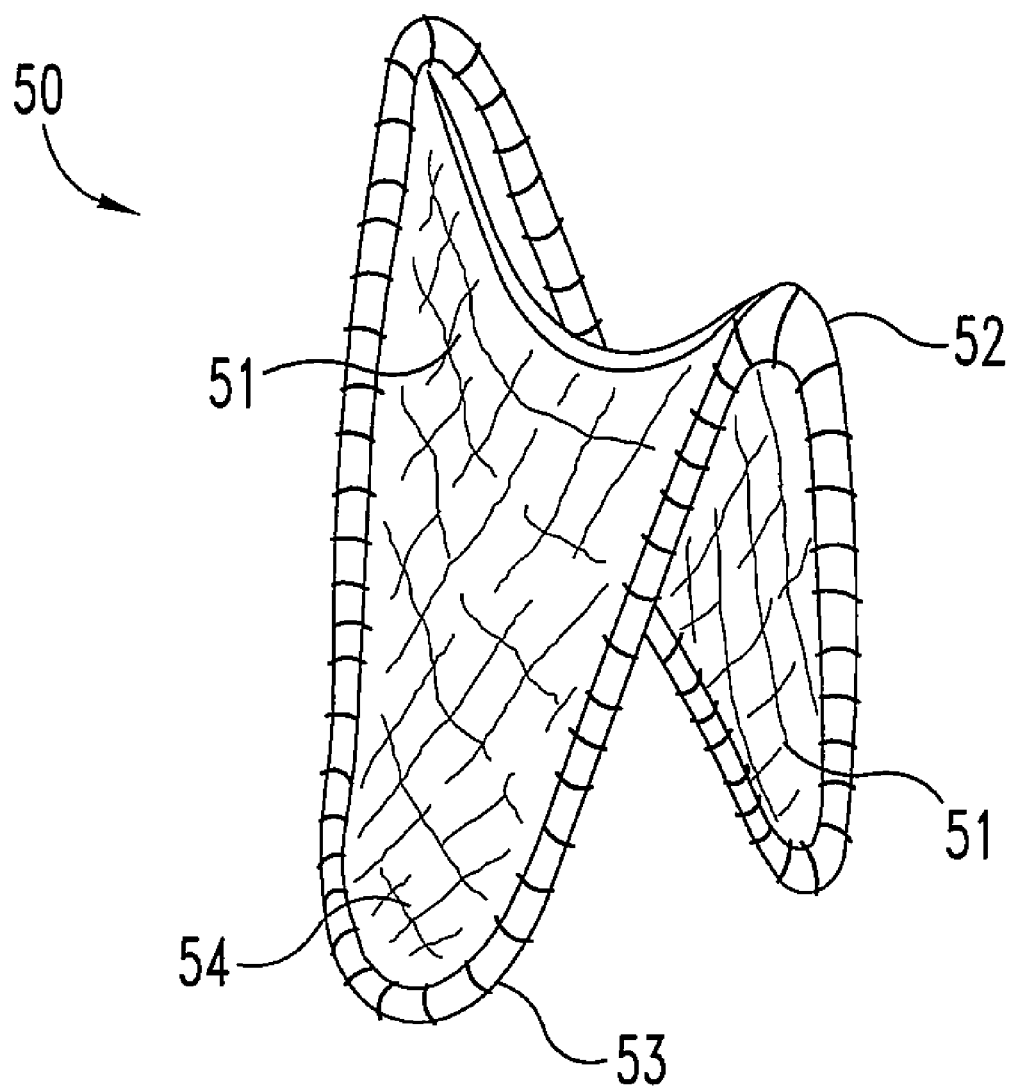
FIG. 5A provides a perspective view of one prosthetic valve of the present invention.

FIG. 5A is a perspective view of an illustrative prosthetic valve 50 of the invention, which includes a pair of leaflets 51 attached to a frame 52, wherein the leaflets comprise a remodeled and then isolated graft material of the invention. The leaflets 51 can be attached to the frame 52 in any suitable manner. For example, in the illustrated embodiment, sutures 53 attach portions of the leaflets' peripheral regions to the frame 52, although it should be noted that other modes of attachment (e.g., adhesives, fasteners, tissue welding using heat and/or pressure, etc.), alone or in combination, are contemplated as well. In other embodiments, the frame 52, or portions thereof, fit into sleeves or pockets formed in peripheral regions of the leaflets 51. Such sleeves can be formed, for example, by rolling up or folding portions of the leaflets' peripheral regions and suturing the material to itself.

Figure 5B:
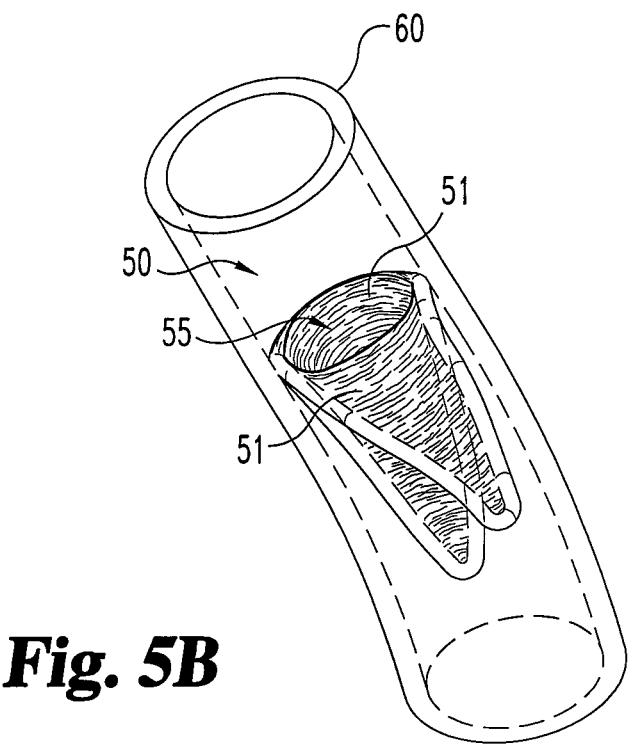
FIG. 5B provides a perspective view of the valve of FIG. 5A implanted within a body passageway, the valve in a generally open configuration.

When the valve is deployed in a body passageway (e.g., at a treatment site within the venous system), the leaflets 51 move back and forth in response to changes in fluid dynamic pressure. When fluid is stagnant or flowing through the passageway in a normal, forward direction, the leaflets 51 remain mostly open (as shown in FIG. 5B). When fluid begins to flow in a direction opposite its normal, forward flow, the leaflets 51 move toward a closed position (as shown in FIG. 5C).

Figure 5C:
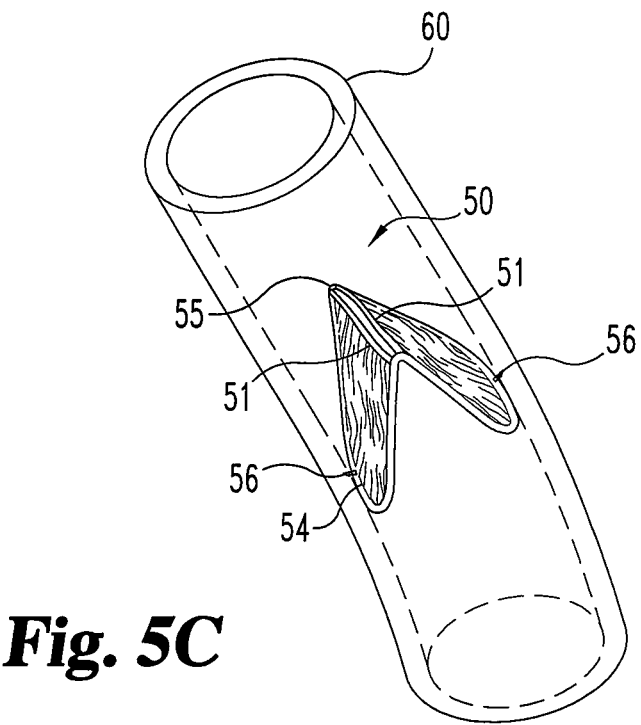
FIG. 5C provides a perspective view of the valve of FIG. 5A implanted within a body passageway, the valve in a generally closed configuration.

Although the embodiment depicted in FIGS. 5A through 5C is a bi-leaflet valve, it should again be noted that the present invention provides for prosthetic valves having one, two, or any practical number of leaflets. For example, bi-leaflet valves may prove advantageous in low-flow venous situations, whereas tri-leaflet embodiments, like those used to replace certain diseased heart valves, may prove advantageous in high-flow situations where thrombosis is far less of a problem.

Continuing with FIG. 5A, it should be noted that after the prosthesis 50 is assembled, the leaflets 51 may be manipulated to alter their shape, size, configuration, and/or orientation. For example, the leaflets 51 may be chemically or otherwise treated to modify the flow dynamics within the prosthesis so that bodily fluid collecting in pockets near bottom portions 54 of the leaflets is more likely to be flushed away or continually mixed with fresher incoming fluid.

The frame 52 depicted in FIG. 5A is only one of many different types of frames that could be utilized in the present invention. Any suitable frame design or style could be used depending on the characteristics desired for a particular application, procedure, technique, and/or patient. For example, in certain embodiments, the prosthetic valve device 50 includes a collapsible frame to facilitate delivery of the valve or to provide other benefits. Such frames, or any portion thereof, may be self-expanding, or alternatively, may be forcibly expandable (e.g. balloon-expandable). In other embodiments, the prosthetic valve 50 includes one or more removable frame elements such as those previously described. Also, the frame 52 can comprise any suitable material. For example, the frame could be formed with a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy).

In addition to metallic materials, a variety of other materials can be used to form the frame 52. Illustratively, a frame material may be selected to suit a particular application (e.g., by considering weight, durability, collapsibility, etc.). In certain embodiments, the frame material is in the form of yarns, fibers, and/or resins, monofilament yarns, high tenacity polyester. Moreover, the present application contemplates other plastic, resin, polymer, woven, and fabric surgical materials, other conventional synthetic surgical materials, such as a shape-memory plastic, and/or combinations of such materials for forming the frame 52. Further, appropriate ceramics can be used, including, without limitation, hydroxyapatite, alumina and pyrolytic carbon.

FIGS. 5B and 5C depict certain prosthetic valve configurations for providing valve function in a body passageway. In particular, FIG. 5B provides a perspective view of the valve device 50 of FIG. 5A implanted or engrafted within a vascular vessel 60, the valve in a generally open configuration. The device 50 can be attached to the vessel 60 in any suitable manner, including but not limited to those previously described. As depicted, the leaflets 51 are configured to move toward and away from one another to close and open, respectively, the valve orifice 55. FIG. 5C provides a perspective view of the valve of FIG. 5A in a generally closed configuration.

The prosthetic valve device 50 can include at least one anchoring element 56 (e.g., a barb) to hold the valve at a general location within a vessel 60. Therefore, while the leaflets 51 are provided to move within the vessel 60 to perform a valving function, the at least one anchoring element 56 generally prevents the valve 50 as a whole from migrating from the implantation site. The at least one anchoring element 56 can be incorporated into or attached to the valve, or any portion thereof, in any suitable manner, including but not limited to suturing, gluing, and the like. Also, suitable anchoring elements can comprise any object, device, or material suitable to attach a cusp to a vessel wall. For example, in certain embodiments, the anchoring element incorporates an adhesive, while in other embodiments, the anchoring element comprises one or more tissue-penetrating attachment elements, such as but not limited to hooks, microbarbs, spurs, claws, prongs, and the like.

Further in this regard, the at least one anchoring element 56 can have any suitable shape, size, and/or orientation to suitably anchor the cusp within the vessel. For example, the anchoring element can adopt a curved configuration and/or can have adaptations to cause it to resist withdrawal from a tissue structure once attached thereto, e.g., in the case of a fish hook-type structure embedded or partially embedded within a vessel wall.

Similarly, the at least one anchoring element 56 can be formed with any suitable biocompatible material, and in some embodiments is formed with a bioresorbable material. In certain other embodiments, an anchoring element is formed with a rigid or semi-rigid synthetic polymeric material, including but not limited to polytetrafluoroethylene (PTFE) (including expanded PTFE) and/or polyethylene terephthalate (PET). In other embodiments, an anchoring element is formed with a rigid or semi-rigid metallic material, including but not limited to, stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). In still other embodiments, an anchoring element is formed with an appropriate ceramic material, including, without limitation, hydroxyapatite, alumina and pyrolytic carbon. Further in this regard, an anchoring element of the invention can include a radiopaque material for positioning and monitoring the prosthesis cusp within a patient.

Prosthetic valve devices of the present invention are desirably adapted for deployment within the vascular system, and in certain preferred embodiments, are adapted for deployment within the venous system. Accordingly, a preferred valve, such as valve 50, can be adapted as a venous valve, for example, for attachment within veins of the legs or feet, to treat venous insufficiency.

Figure 6A:
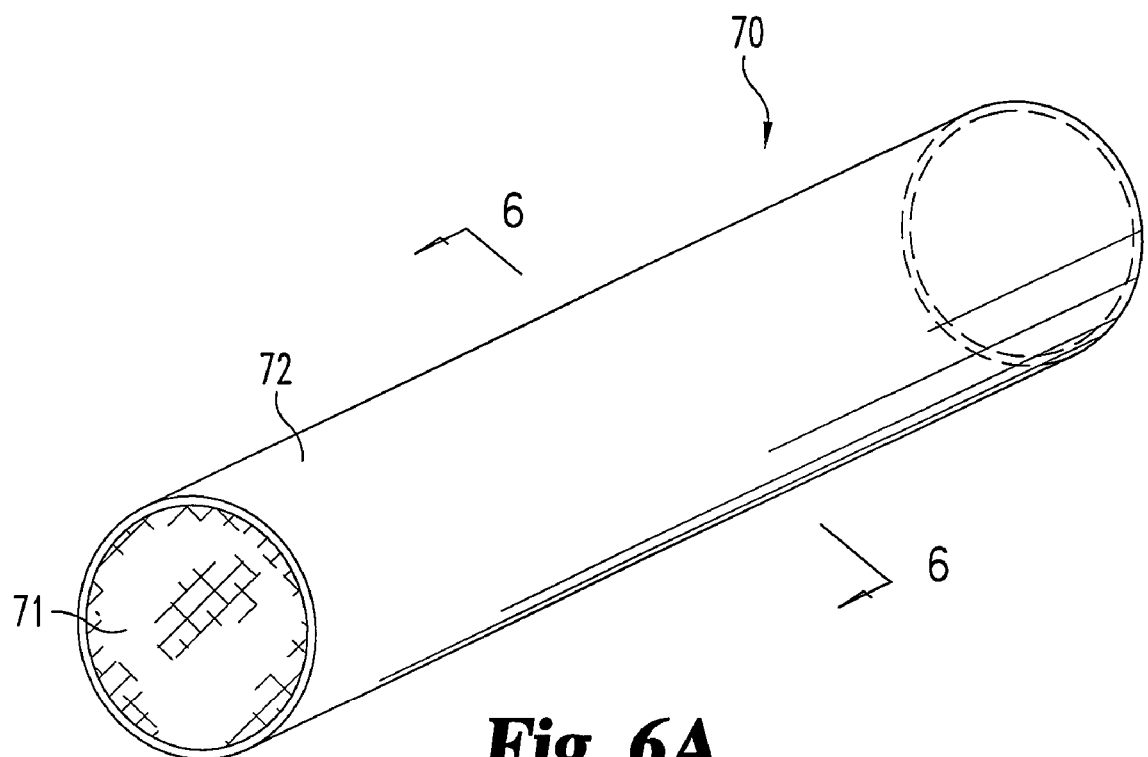
FIG. 6A provides a perspective view of another prosthesis-forming device of the present invention.
Figure 6B:
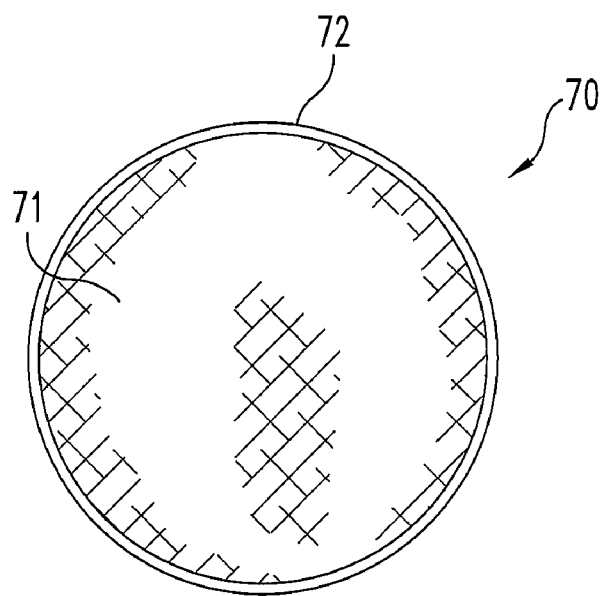
FIG. 6B provides a front view of the device of FIG. 6A along the view line 6-6 shown in FIG. 6A.

With reference now to FIGS. 6A and 6B, shown are a perspective view and a cross-sectional view, respectively, of an illustrative prosthesis-forming device 70 of the present invention, which includes an amount of remodelable material 71 received within and filling a tubular form 72. In particularly preferred embodiments, the amount of remodelable material 71 comprises submucosa, e.g., small intestinal submucosa.

Like before, the prosthesis-forming device 70 can be inserted into a body cavity, allowed to remodel through the inner lumen of the form 72, and thereafter removed and optionally manipulated to provide a prosthetic device in accordance with the present invention. If desired, form 72 can be provided with perforations or holes, or can be made with a porous mesh or screen material, to allow further access of local biological factors and cells to the material 71 during the residence period. In particularly preferable embodiments, at least a portion of the at least partially remodeled material is separated or extracted from the form 72 to provide a solid, elongate body of graft material suitable for implantation within a patient. For example, this solid elongate body of graft material can be adapted to provide a prosthetic ligament or tendon of any suitable size, shape, and or configuration. Such a graft body could also be configured as an implant for bulking and/or augmentation purposes.

Figure 7A:
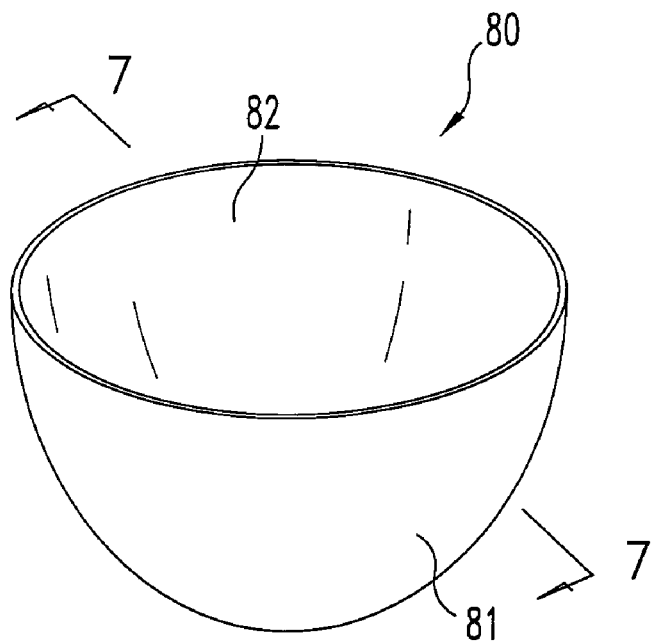
FIG. 7A provides a perspective view of another prosthesis-forming device of the present invention.
Figure 7B:
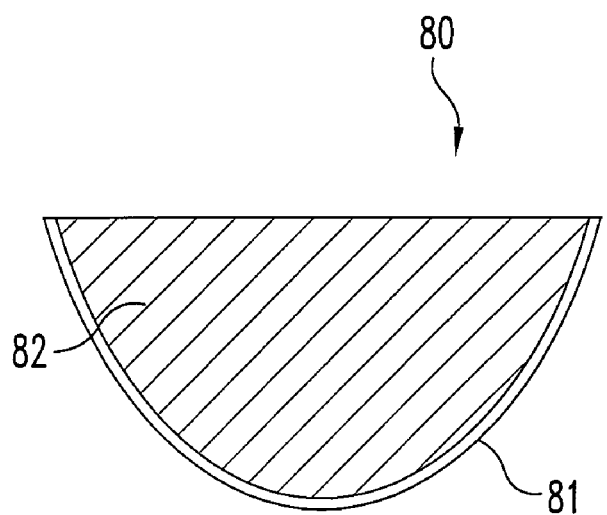
FIG. 7B provides a front view of the device of FIG. 7A along the view line 7-7 shown in FIG. 7A.

FIGS. 7A and 7B provide a perspective view and a cross-sectional view, respectively, of an illustrative prosthesis-forming device 80 of the present invention, which includes a thin sheet of remodelable material 81 attached to the bottom, outer surface of a bowl-shaped form 82. Using the methods described above, this prosthesis-forming device 80 can be used to provide an implantable grafting device in accordance with the present invention, for example, a grafting device adapted for use in a joint, e.g., a ball-and-socket joint such as a hip or shoulder.

The present invention also provides a line of medical product, wherein a medical product of the invention includes an amount of remodeled, isolated graft material in a sealed package. The amount of graft material can comprise at least one segment or piece of the graft material and/or at least one of the grafting devices disclosed herein. When a plurality of segments and/or devices is included, the segments and/or devices can each be of substantially the same size and shape, or, alternatively, can vary with respect to size and shape.

Figure 8:
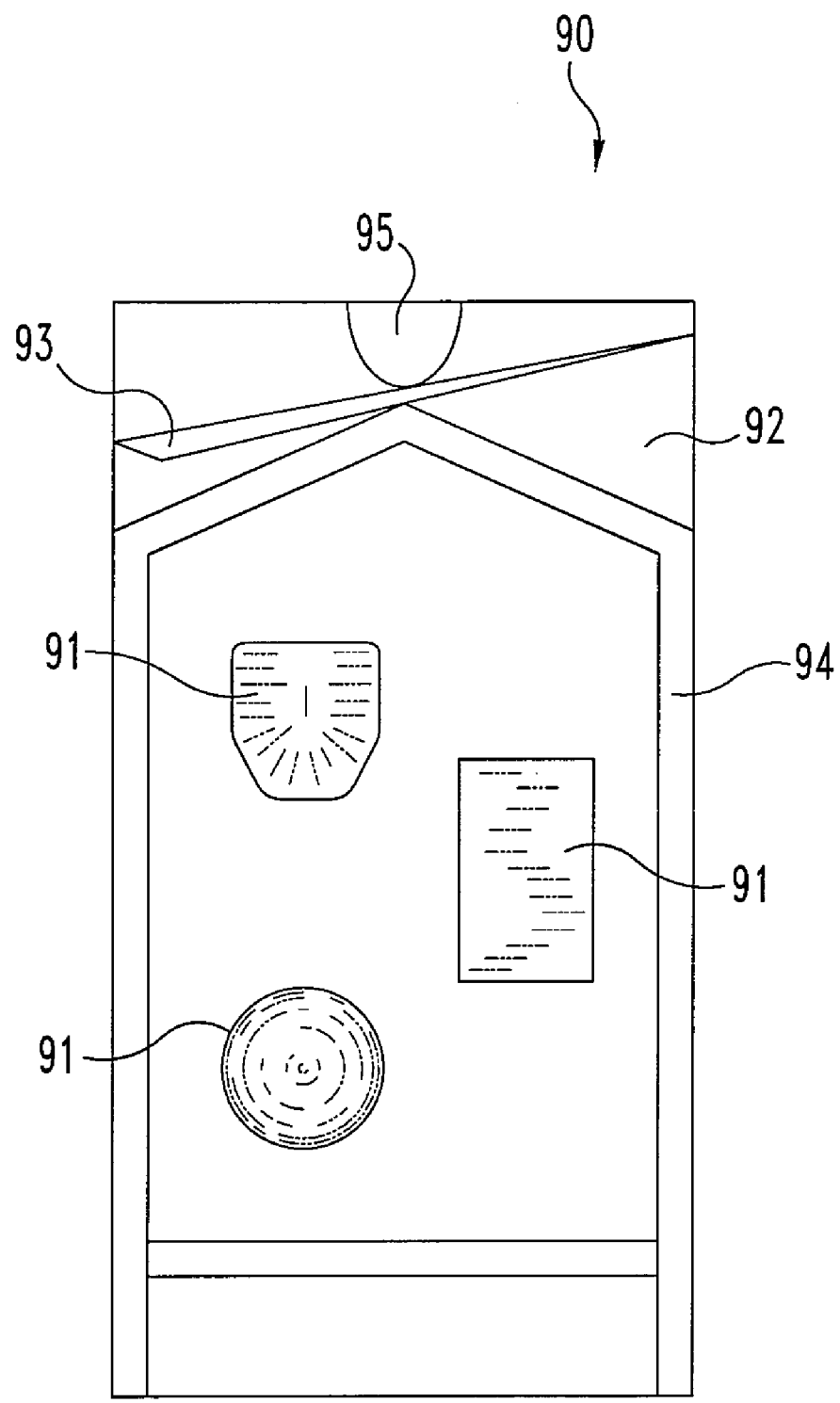
FIG. 8 provides a top view of a medical product of the present invention.

With reference now to FIG. 8, shown is a top view of an illustrative medical product 90 of the present invention that includes an amount of graft material 91 sealed within sterile medical packaging. In particular, the medical product has packaging including a backing layer 92 and a front film layer 93 (shown partially drawn away from backing layer 92). The amount of graft material 91 is sealed between backing layer 92 and film 93 utilizing a boundary of pressure-adhesive 94 as is conventional in medical packaging. A cut-out 95 may be provided in the backing layer 92 to assist a user in separating the film layer 93 from the backing layer 92.

Terminal sterilization of the medical product 90 may be achieved, for example, by irradiation, ethylene oxide gas, or any other suitable sterilization technique, and the materials and other properties of the medical packaging will be selected accordingly. Also, graft material of the invention can be contained in a sterile packaging in any suitable state. Suitable states include, for example, a hydrated or dehydrated state. The graft material can be dehydrated by any means known in the art (e.g., lyophilization or air dried). If graft material of the present invention is stored in a dehydrated state, it is preferred that it retains all of its biological and mechanical properties (e.g., shape, density, flexibility, etc.) upon rehydration.

Additionally, the package can include indicia to communicate the contents of the package to a person, machine, computer, and/or electronic device. Such indicia may include the dimensions of, the type of materials used to form, and/or the physical state of, the contents of the package. In certain embodiments, the graft material or grafting device is packaged for sale with instructions for use. For example, in certain preferred embodiments, a medical product includes at least one prosthetic vascular valve sealed within a sterile package, wherein the packaging can have visible indicia identifying the at least one valve as a venous or other vascular valve, and/or can contain or otherwise be associated with printed materials identifying the contents as a venous or other vascular valve and including information concerning its use as a venous or other vascular valve. The packaging could also include visible indicia relating to the dimension of the at least one valve, and/or relating to the vessel diameter(s) for which the at least one valves is configured.

Figure 9:
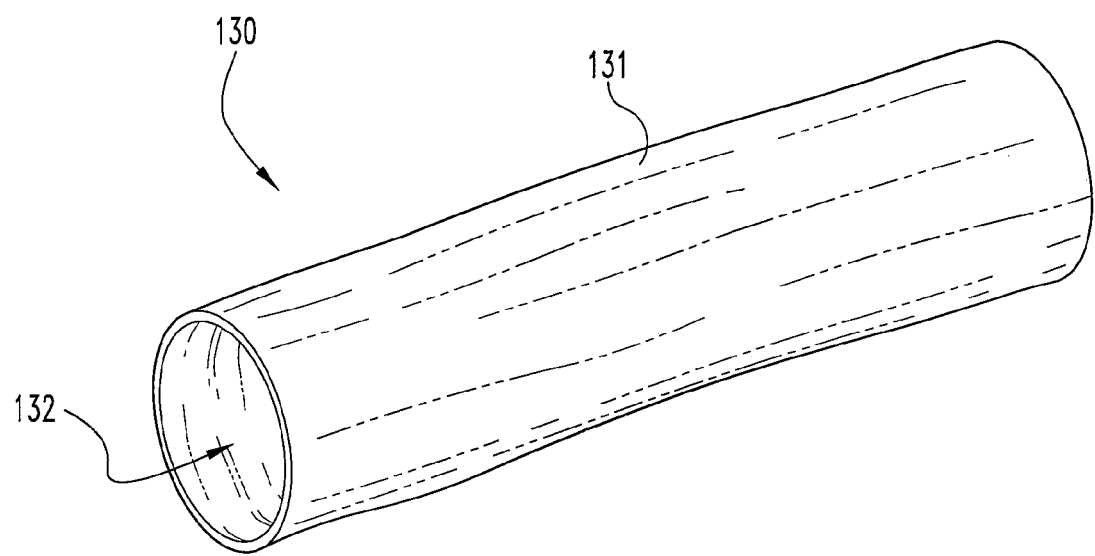
FIG. 9 provides a perspective view of a graft device of the invention.

FIG. 9 provides a perspective view of a tube of remodeled tissue material 130 in accordance with the present invention. Tube 130 includes a generally cylindrical wall 131 defining an interior lumen 132. A tube of remodeled tissue material such as tube 130 can be prepared in a variety of manners, for example, including those described above in relation to FIGS. 3A and 3B. (Similarly, the construct depicted in FIG. 9 could also represent a tube of remodelable material insertable into a body cavity to be remodeled, whether essentially by itself or in combination with one or more other insertable objects).

As will be appreciated by those skilled in the art, a remodeled tubular construct such as tube 130 has a broad range of uses. In some forms, such a tube is placed in the body to replace a circulation vessel, or a portion thereof, or to bypass a blocked vessel, or to line a vascular or other vessel, e.g., a vein or an artery, or to otherwise suitably treat a patient. These sorts of tubes can be treated or otherwise processed in any suitable manner including those described herein, for example, disinfected, decellularized, crosslinked, etc. In accordance with one embodiment of the invention, the interior (luminal) surface of tube 130 is populated with endothelial cells, preferably vascular endothelial cells. At least one additional exogenous cell population, preferably muscle cells such as smooth muscle cells, and/or fibroblasts, can also be included on the construct. Such tissue grafts provide advanced functionality and durability beneficial to replacement vessels for use in patients, including human patients.

In certain embodiments, a remodeled tubular construct such as tube 130, once isolated from the body cavity, is attached to or otherwise associated with one or more other implantable objects (e.g., valves, stents, anchoring devices, etc.) prior to being implanted in an implant recipient. When remodeled tissue material is attached to such a device, any suitable mode of attachment may be utilized including but not limited to suturing, bonding with an adhesive, welding and suitable combinations and variations thereof. Some of these implantable devices are expandable or at least have an expandable element. Illustratively, an inventive stent graft device can include a tube of remodeled graft material and an expandable stent, wherein at least a portion of the stent is embedded within the tube of remodeled graft material. In one embodiment, such a device is prepared by inserting into a body cavity a remodelable material in combination with an expandable stent, e.g., with the stent in an expanded configuration. After a suitable residence time, the stent-remodeled material device is removed from the body cavity and optionally disinfected and/or otherwise prepared for implantation in an implant recipient. In some cases, such a device is contracted for positioning in a delivery device lumen for delivery into the body.

Illustratively, an implantable device, when incorporated into a graft device of the invention, may be any one of wide variety of stent devices that have been or are currently commercially available. Stent devices provide a supporting framework structure that may take many forms. Open or perforated stents are known, which may include a network of struts or wire-like elements. Such devices can be configured for and used in a variety of bodily lumens, including as examples those in the vascular system such as arteries and veins, urethra, ureter, bile duct, trachea, esophagus, bowel, and others.

When utilized in the invention, stent devices may be of any suitable design, including for example both forcibly expandable and self-expanding stems. As is known, forcibly expandable stents can be provided and delivered in a contracted state, and then expanded upon the application of a force, e.g. an outward radial force, to the stent. Commonly, the outward radial force is provided by an expandable member, such as a balloon, received within the contracted stent structure. Several such "balloon-expandable" stents are currently available on the commercial market. Self-expanding stents can be designed so as to be configurable to and held in a contracted state for delivery, and then released at a target site, whereupon they expand on their own. Stents are also known that take on a contracted state, but expand in response to a conditional change, e.g., a change in temperature such as may be incurred in a temperature transition from a first temperature below the body temperature of a patient, to the body temperature of the patient. Stents having these or other characteristics may be used in embodiments of the present invention.

Stents or other similar expandable or non-expandable support members may be made from metallic or non-metallic material, or both. The non-metallic material can suitably be a synthetic polymeric material, including for example bioresorbable and/or non-bioresorbable plastics. Materials commonly used in stent construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

Just to identify a few non-limiting examples, suitable stents for use in the invention include the Silver stent, Gianturco-Roubin stent, the Palmaz-Schatz stent, Wallstent, Mammotherm stent, Symphony stent, Smart stent, Perflex, AVE, Intrastent, and Herculink stems, self-expanding Instent, Gianturco Z-stent, Ultraflex nitinol mesh stent, Esophacoil stent, Gianturco Z tracheobronchial tree stent, and the Wallstent tracheobronchial endoprosthesis.

Certain embodiments of the invention provide medical devices including an expandable member, e.g., as described above, associated with a full or partial covering of material on an inner and/or outer surface of the expandable member. Thus, in one aspect, such a covering material is formed with a remodelable material that can remodel when inserted into a body cavity as described elsewhere herein. Additionally or alternatively, such a covering material can include tissue material that has already been remodeled in accordance with the present invention. In some embodiments, the covering material is associated in a unique manner with the expandable member. For example, the covering material may be contoured snugly around or completely embed elements of the expandable member to assist in maintaining the attachment of the covering material to the expandable member. This may avoid, reduce, or simplify the need for other mechanical attachments, such as sutures, to hold the covering material to the expandable member. It may also in some forms provide a unique, relatively fixed association of the covering material with the expandable member or elements thereof, even during contraction and/or expansion of the expandable member.

In some embodiments, the invention provides a graft device that includes a plurality of discrete, spaced stents. The discrete, spaced stents are interconnected to one another by inner and/or outer layers of material. At least one of (and potentially both of) the inner and outer layers can include a multilaminate material. In one aspect, the invention provides a graft device that includes a plurality of discrete, spaced stents interconnected to one another by inner and outer layers of material. The inner and outer layers can be bonded to one another and entrap and interconnect the discrete, spaced stents. In certain embodiments, at least one of (and potentially both of) the inner and outer layers includes a multilaminate construct, and/or the inner and outer layers are dehydrothermally bonded to one another, e.g. by vacuum pressing and/or lyophilization conditions.

Figure 10:
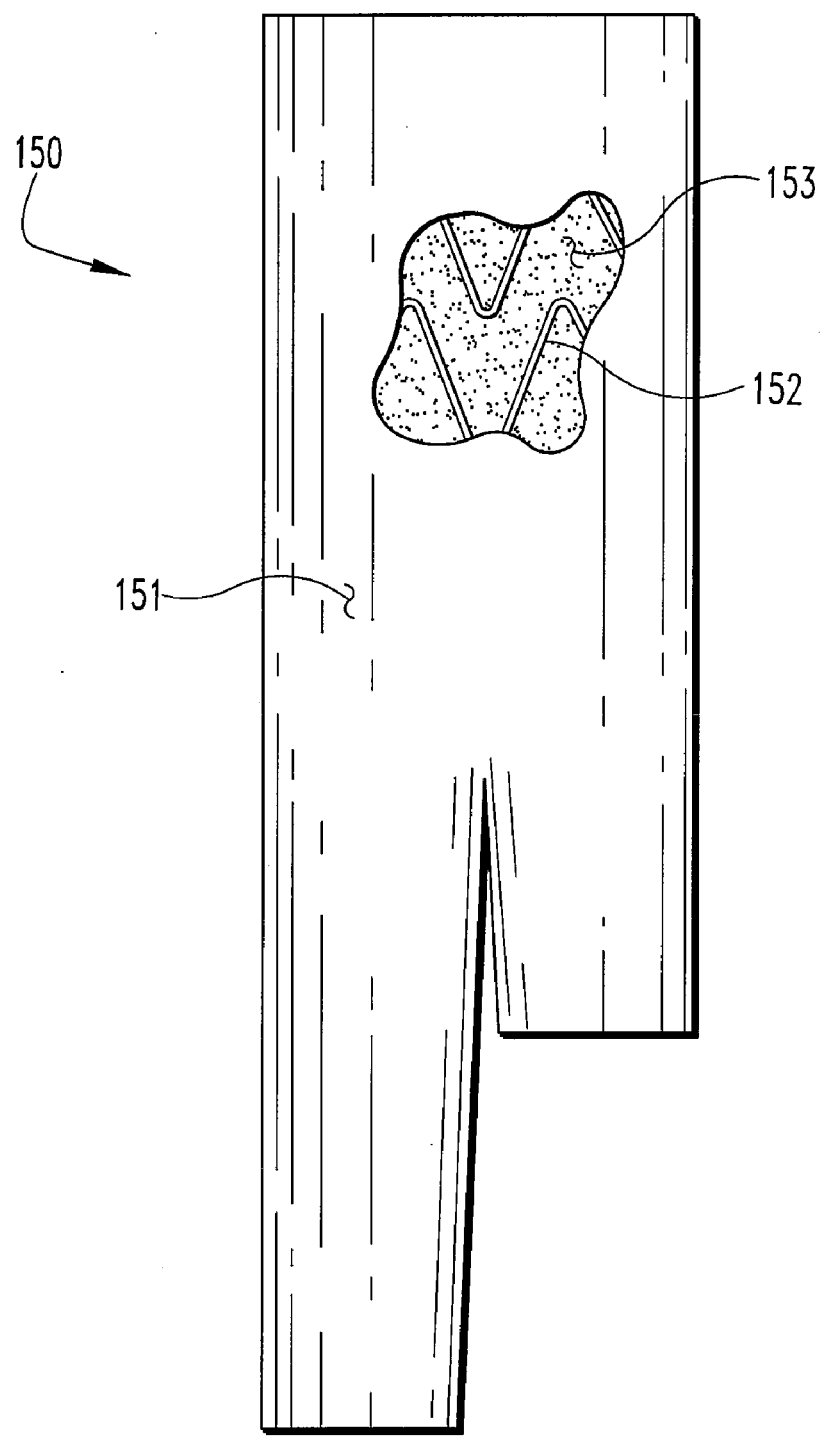
FIG. 10 provides a partial cut-away perspective view of another graft device of the invention.

FIG. 10 provides a partial cut-away perspective view of a stent graft device 150 of the invention. Device 150 includes a first, larger lumen that directs its flow into two smaller lumens, as illustrated. Device 150, in this regard, may be generally similar to the graft body provided in the Zeniths endovascular graft available from Cook, Inc. Bloomington, Ind. Device 150, however, can include an outer covering material 151, and/or an inner covering material 153, in combination with a plurality of stents 152 including generally serpentine elements, in a manner or to have a character as described in connection with some of the embodiments described herein. Thus, in one aspect, covering materials useful in the invention such as outer covering material 151 and/or inner covering material 152 are formed with a remodelable material that can remodel when inserted into a body cavity as described elsewhere herein. Additionally or alternatively, such covering materials can include tissue material that has already been remodeled in accordance with the present invention and thereafter combined with the plurality of stents.

In stent graft device 150 and potentially in other stent graft designs disclosed herein, a plurality of separate and discrete stent elements (e.g. 152) can be interconnected by the covering material and entrapping, bonding and other methods described herein to form a unitary graft device, representing additional aspects of the invention. Such interconnections can be achieved by any suitable methods, and may include the use of inner and outer covering material layers that are single or multilaminate constructs, e.g. multilaminate bioremodelable ECM or other constructs as described herein. In this regard, the lamination of the layers in the multilaminate constructs can occur prior to and/or during the application of the covering materials to the stented graft constructs of the invention. In some cases, multiple layers of remodelable material inserted into a body cavity to be remodeled can become at least somewhat adhered to one another as remodeling occurs. As well, any suitable arrangement of one or more pieces of covering material that results in a stable interconnection of the stents may be used. In this regard, a single tube or other piece of covering material could be wrapped inside and outside the multiple stents to interconnect them, separate tubes or other pieces (each tube or piece single or multilaminate) could be used inside and/or outside, etc. Furthermore, it would not be necessary for any single piece to extend completely between any two of the stents in the assembly (although this is certainly possible and advantageous in some respects), as covering material pieces contacting respective spaced stents could be arranged to overlap one another in regions spanning between the spaced stents and nonetheless provide for an effective interconnection of the stents in the final construct. As to the number of stents in the overall construct, this will depend upon the intended application of the final device and required properties; however, constructs having anywhere from two to thirty or more stents, which may be the same or may differ from one another and may be radially expandable or fixed, are contemplated as being a part of the present invention. These and other alternatives will be apparent to those skilled in the art from the descriptions herein.

The present invention further provides a method of treating atherosclerosis or other blood vessel disease, the method comprising by-passing or replacing the damaged blood vessel by grafting a prosthetic blood vessel of the present invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An isolated graft material retaining a valve cusp shape for providing a valve cusp for contacting and modifying fluid flow in a body passageway, said isolated graft material prepared by a process comprising removing from a body cavity of a host a tissue material resulting from remodeling of a previously inserted amount of a remodelable extracellular matrix material in the body cavity, the remodelable extracellular matrix material being associated with an implanted shaping element in the body cavity and being effective, upon insertion in said body cavity, to stimulate the ingrowth of native cells into the remodelable extracellular matrix material such that the remodelable extracellular matrix material becomes infiltrated and replaced by newly formed host tissue, wherein said remodeling of said previously inserted amount of remodelable extracellular matrix material in association with said implanted shaping element causes said graft material to retain said valve cusp shape.

2. The isolated graft material of claim 1, wherein said remodelable extracellular matrix material retains bioactive components native to a source tissue for the extracellular matrix material.

3. The isolated graft material of claim 2, wherein said remodelable extracellular matrix material comprises at least 80% by weight collagen on a dry weight basis, includes uniaxial or multiaxial oriented fibers, and includes at least about 3% retained non-collagenous solids from the source tissue, the non-collagenous solids including said bioactive components.

4. The isolated graft material of claim 2, wherein the bioactive components comprise growth factors.

5. The isolated graft material of claim 1, wherein said remodelable extracellular matrix material includes a section that is held in tension against a surface of said implanted shaping element in said body cavity.

6. The isolated graft material of claim 1 coupled to an implantable valve frame.

7. The isolated graft material of claim 1 further providing a generally hollow, tubular graft which incorporates said valve cusp within said tubular graft.

8. The isolated graft material of claim 1, wherein said remodelable extracellular matrix material is further associated with a frame element in said body cavity.

9. A method of forming an isolated graft material suitable for implantation in the body of a patient, the method comprising removing from a body cavity of a host a tissue material resulting from remodeling of a previously inserted amount of a remodelable extracellular matrix material in the body cavity, the remodelable extracellular matrix material being associated with an implanted shaping element in the body cavity and being effective, upon insertion in said body cavity, to stimulate the ingrowth of native cells into the remodelable extracellular matrix material such that the remodelable extracellular matrix material becomes infiltrated and replaced by newly formed host tissue, wherein said remodeling of said previously inserted amount of remodelable extracellular matrix material in association with said implanted shaping element causes said tissue material to retain a valve cusp shape for providing a valve cusp for contacting and modifying fluid flow in a body passageway, or an elongate generally cylindrical shape having a generally solid cross section for providing a prosthetic ligament or tendon.

10. The method of claim 9, wherein the tissue material is removed from the body cavity at least 15 days after being inserted therein.

11. The method of claim 9, wherein the tissue material is removed from the body cavity no later than 45 days after being inserted therein.

12. The method of claim 9, wherein the tissue material is removed from the body cavity at least 25 days after being inserted therein.

13. The method of claim 9, wherein said remodelable extracellular matrix material retains bioactive components native to a source tissue for the extracellular matrix material.

14. The method of claim 13, wherein said remodelable extracellular matrix material comprises at least 80% by weight collagen on a dry weight basis, includes uniaxial or multiaxial oriented fibers, and includes at least about 3% retained non-collagenous solids from the source tissue, the non-collagenous solids including said bioactive components.

15. A method of forming an isolated, decellularized tissue material, the method comprising:
removing from a body cavity of a host a tissue material resulting from remodeling of a previously inserted amount of a remodelable extracellular matrix material in the body cavity, the remodelable extracellular matrix material being effective, upon insertion in said body cavity, to stimulate the ingrowth of native cells into the remodelable extracellular matrix material such that the remodelable extracellular matrix material becomes infiltrated and replaced by newly formed host tissue; and
decellularizing the tissue material following removal from said body cavity.

16. The method of claim 15, wherein said tissue material is in the form of a sheet.

17. The method of claim 15, wherein said tissue material is in the form of a tube.

18. The method of claim 17, wherein said tube is hollow.

19. The method of claim 15, wherein said tissue material provides one or more valve leaflets.

20. The method of claim 15, wherein said tissue material is in the form of a prosthetic ligament or tendon.

21. The method of claim 15, wherein said remodelable extracellular matrix material was seeded with one or more cell populations prior to being inserted in said body cavity.

22. The method of claim 15, wherein said remodelable extracellular matrix material is associated with a frame element in said body cavity.

23. The method of claim 22, wherein said frame element comprises one or more stents.

24. The method of claim 23, wherein said one or more stents includes a plurality of discrete, spaced stents which are embedded within and interconnected to one another by said tissue material.

25. The method of claim 15, wherein said isolated, decellularized tissue material is adapted for implantation in a joint.

26. The method of claim 15, wherein said body cavity is that of a vertebrate.

27. The method of claim 26, wherein said body cavity is that of a bovine, equine, ovine, or porcine.

28. The method of claim 26, wherein said body cavity is that of a human.

29. The method of claim 15, wherein said body cavity is a peritoneal cavity.

30. The method of claim 15, wherein said body cavity is a thoracic cavity, scrotum, brain, joint, or pericardial cavity.

31. The method of claim 15, wherein said remodelable extracellular matrix material is associated with an implanted shaping element in the body cavity.

32. The method of claim 31, wherein said implanted shaping element is biodegradable.

33. The method of claim 31 further comprising separating said shaping element from said graft material after said graft material is removed from said body cavity.

34. The method of claim 31, wherein said isolated, decellularized tissue material retains a valve cusp shape for providing a valve cusp for contacting and modifying fluid flow in a body passageway.

35. The method of claim 15, wherein said remodelable extracellular matrix material is located inside a shaping mold in said body cavity.

36. The graft material of claim 35, wherein a wall of said shaping mold is perforated to allow fluid access through said wall.

37. The method of claim 35, wherein said shaping mold comprises a hollow tubular mold.

38. The method of claim 37, wherein said remodelable extracellular matrix material is received within and fills said hollow tubular mold.

39. The method of claim 15, wherein said isolated, decellularized graft material provides an elongate graft body having a generally solid cross section for providing a prosthetic ligament or tendon.

40. The method of claim 15, wherein said remodelable extracellular matrix material comprises a sheet of remodelable extracellular matrix material obtained in sheet form from a collagenous tissue source.

41. The method of claim 40, wherein said remodelable extracellular matrix sheet material retains bioactive components native to a source tissue for the extracellular matrix sheet material.

42. The method of claim 41, wherein said remodelable extracellular matrix sheet material comprises at least 80% by weight collagen on a dry weight basis, includes uniaxial or multiaxial oriented fibers, and includes at least about 3% retained non-collagenous solids from the source tissue, the non-collagenous solids including said bioactive components.

43. The method of claim 40, wherein said remodelable extracellular matrix sheet material includes a section that is held in tension against a surface of an implanted shaping element in said body cavity.

44. The method of claim 43, wherein said surface is generally cylindrical.

45. The method of claim 43, wherein said surface is generally planar.

46. The method of claim 43, wherein said section, when held in tension against said surface of said implanted shaping element, takes the shape of a valve cusp.

47. The method of claim 46, wherein said valve cusp shape is maintained during remodeling of the remodelable extracellular matrix material such that said valve cusp shape is generally retained by said section after removal from the body cavity.

48. An isolated tissue material suitable for implantation in the body of a patient, said isolated tissue material prepared by a process comprising removing from a body cavity of a host a tissue material resulting from remodeling of a previously inserted amount of a remodelable extracellular matrix material in the body cavity, the remodelable extracellular matrix material being associated with an implanted shaping element in the body cavity and being effective, upon insertion in said body cavity, to stimulate the ingrowth of native cells into the remodelable extracellular matrix material such that the remodelable extracellular matrix material becomes infiltrated and replaced by newly formed host tissue, wherein said remodeling of said previously inserted amount of remodelable extracellular matrix material in association with said implanted shaping element causes said tissue material to retain a valve cusp shape for providing a valve cusp for contacting and modifying fluid flow in a body passageway, or an elongate generally cylindrical shape having a generally solid cross section for providing a prosthetic ligament or tendon.

49. The isolated tissue material of claim 48, wherein said remodelable extracellular matrix material comprises serosa, pericardium, submucosa, dura mater, peritoneum, or dermal collagen.

50. The isolated tissue material of claim 48, wherein said tissue material comprises said remodelable extracellular matrix material remodeled in said body cavity.

51. The isolated tissue material of claim 48 further comprising mesothelial cells from said body cavity.

52. The isolated tissue material of claim 48 further comprising myofibroblasts from said body cavity.

53. The isolated tissue material of claim 48 provided in a decellularized state.

* * * * *